US010596190B2

(12) United States Patent
Neuwelt

(10) Patent No.: US 10,596,190 B2
(45) Date of Patent: Mar. 24, 2020

(54) METHOD FOR REDUCING OTOTOXICITY IN PEDIATRIC PATIENTS RECEIVING PLATINUM-BASED CHEMOTHERAPY

(71) Applicant: Edward A. Neuwelt, Portland, OR (US)

(72) Inventor: Edward A. Neuwelt, Portland, OR (US)

(73) Assignee: Oregon Health & Science University, Portland, OR (US)

(*) Notice: Subject to any disclaimer, the term of this patent is extended or adjusted under 35 U.S.C. 154(b) by 37 days.

(21) Appl. No.: 16/112,195

(22) Filed: Aug. 24, 2018

(65) Prior Publication Data

US 2019/0160094 A1 May 30, 2019

Related U.S. Application Data

(63) Continuation of application No. 15/826,243, filed on Nov. 29, 2017, now abandoned.

(51) Int. Cl.
*A61K 33/04* (2006.01)
*A61P 39/00* (2006.01)
*A61P 27/16* (2006.01)

(52) U.S. Cl.
CPC .............. *A61K 33/04* (2013.01); *A61P 27/16* (2018.01); *A61P 39/00* (2018.01)

(58) Field of Classification Search
None
See application file for complete search history.

(56) References Cited

U.S. PATENT DOCUMENTS

| 7,022,315 | B2 | 4/2006 | Neuwelt |
| 8,496,973 | B2 | 7/2013 | Sherman |
| 2004/0062764 | A1 | 4/2004 | Neuwelt et al. |
| 2014/0147516 | A1 | 5/2014 | Hayden et al. |
| 2014/0302179 | A1 | 10/2014 | Sherman et al. |
| 2017/0182089 | A1 | 6/2017 | Neuwelt et al. |

OTHER PUBLICATIONS

Sullivan, Cancer 5623-5626 (2009) (Year: 2009).*
Xu et al. Nature Genetics 47(3), 263-266 (2015) (Year: 2015).*
Brock Meeting News Coverage ASCO Annual Meeting (Jun. 2, 2015) https://www.healio.com/hematology-oncology/pediatric-oncology/news/online/%7Bac050c68-7e30-4904-a239-404a14429c6c%7D/ (retrieved from the internet Dec. 11, 2018) (Year: 2015).*
NCT00652132 (2005) https://clinicaltrials.gov/ct2/show/NCT00652132 (retrieved from the internet Dec. 11, 2018) (Year: 2015).*
SIOPEL guidelines for the treatment of hepatoblastoma at http://www.siopel.org/?q=node/157 (2015) (retrieved from the internet Jun. 18, 2019) (Year: 2015).*
Muldoon et al. In Clinical Cancer Research 6, 309-315 (2000) (Year: 2000).*

Brock, P. R. et al., 'Sodium thiosulfate for protection from cisplatin-induced hearing loss', New England Journal of Medicine, Jun. 21, 2018, vol. 378, No. 25, pp. 2376-2385.
International Search Report dated May 27, 2019, prepared in International Application No. PCT/US2018/062750.
Written Opinion dated May 27, 2019, prepared in International Application No. PCT/US2018/062750.
Brock, Penelope R., et al. "Platinum-Induced Ototoxicity in Children: A Consensus Review on Mechanisms, Predisposition, and Protection, Including a New International Society of Pediatric Oncology Boston Ototoxicity Scale", Journal of Clinical Oncology, vol. 30, No. 19, Jul. 1, 2012, pp. 2408-2417 (Published Online ahead of print www.Jco.Org on Apr. 30, 2012.
Freyer, David, R., "Effects of sodium thiosulfate versus observation on development of cisplatin-induced hearing loss in children with cancer (ACCL0431): a multicentre, randomised, controlled, open-label, phase 3 trial", www.thelancet.com/oncology Published online Nov. 30, 2016, http://dx.doi.org/10.1016/S1470-2045(16)30625-8.
Freyer, David R., "Reducing cisplatin ototoxicity in children: some hope and many questions" www.thelancet.com/oncology, published online Nov. 30, 2016, http://dx.doi.org/10.1016/S1470-2045(16)30630-1—Comment Bouffet, Eric., The Hospital for Sick Children, University of Toronto.
Frisina, Robert D., et al. "Comprehensive Audiometric Analysis of Hearing Impairment and Tinnitus After Cisplatin-Based Chemotherapy in Survivors of Adult-Onset Cancer", Journal of Clinical Oncology, Published online ahead of print at www.jco.org on Jun. 27, 2016, Information downloaded from jco.ascopubs.org and provided by at Oregon Health & Science University on Aug. 1, 2016.
Gurney, J.G. et al., "New International Society of Pediatric Oncology Boston Ototoxicity Grading Scale for Pediatric Oncology: Still Room for Improvement" Oncology, J. Clin. Onc. , 2012, vol. 30, No. 19, pp. 2303-2306.
Neuwelt, Edward A. et al., "First Evidence of Otoprotection Against Carboplatin-Induced Hearing Loss with a Two-Compartment System in Patients with Central Nervous System Malignancy Using Sodium Thiosulfate" The Journal of Pharmacology and Experimental Therapeutics, 1998, vol. 286, No. 1, pp. 77-84.
Neuwelt, Edward A., et al., "Toxicity Profile of Delayed High Dose Sodium Thiosulfate in Children Treated with Carboplatin in Conjunction with Blood-Brain-Barrier Disruption", Pediatr Blood Cancer 2006, vol. 47, pp. 174-182.
Neuwelt, Edward A., et al., "In Vitro and Animal Studies of Sodium Thiosulfate as a Potential Chemoprotectant against Carboplatin-induced Ototoxicity", Cancer Research, Feb. 15, 996, vol. 56, pp. 706-709.
Pussegoda, K. et al Replication of TPMT and ABCC3 Genetic Variants Highly Associated With Cisplatin-Induced Hearing Loss in Children, Clin. Pharmacol. Ther., 2013, vol. 94, pp. 243-251.
Xu, K. et al., "Common variants in ACYP2 influence susceptibility to cisplatin-induced hearing loss", Nat.Genetics. 2015, vol. 47, No. 3, pp. 263-266.
Ross, Colin J.D., et al. "Genetic variants in TPMT and COMT are associated with hearing loss in children receiving cisplatin chemotherapy", Nature Genetics, Dec. 2009, vol. 41, No. 12. pp. 1345-1350.

* cited by examiner

*Primary Examiner* — Dennis Heyer
(74) *Attorney, Agent, or Firm* — Barnes & Thornburg LLP

(57) ABSTRACT

Described herein is a method for eliminating or reducing ototoxicity in patients receiving a platinum based chemotherapeutic. In particular, are methods of reducing ototoxicity in a pediatric patient. The methods described herein include administering an effective amount of sodium thiosulfate to a patient in need thereof to reduce ototoxicity.

1 Claim, 42 Drawing Sheets

FIG. 2

| Characteristic | Observation (%) | STSJCA |
|---|---|---|
| Eligible | 64 | 62 |
| Age at enrollment (yrs) | | |
| < 5 | 22 (34.4) | 22 (35.5) |
| ≥ 5 | 42 (65.6) | 40 (64.5) |
| Sex | | |
| Male | 41 (64.1) | 35 (56.5) |
| Female | 23 (35.9) | 27 (43.5) |
| Race | | |
| White | 39 (60.9) | 43 (69.4) |
| Black | 10 (15.6) | 5 (8.1) |
| Other/Unknown | 15 (23.4) | 14 (22.6) |
| Ethnicity | | |
| Non-Hispanic | 46 (71.9) | 41 (66.1) |
| Hispanic | 18 (28.1) | 21 (33.9) |

FIG. 3

| Characteristic | Observation (%) | STS (%) |
|---|---|---|
| Diagnosis | | |
| Germ Cell Tumor | 16 (25.0) | 16 (25.8) |
| Osteosarcoma | 15 (23.4) | 15 (24.2) |
| Medulloblastoma | 14 (21.9) | 12 (19.4) |
| Neuroblastoma | 12 (18.8) | 14 (22.6) |
| Hepatoblastoma | 5 (7.8) | 2 (3.2) |
| Other | 2 (3.1) | 3 (4.8) |
| Extent of Disease | | |
| Localized | 38 (59.4) | 40 (64.5) |
| Disseminated | 26 (40.6) | 21 (33.9) |
| Unknown | 0 | 1 (1.6) |
| Cum. CDDP dose (mg/m$^2$) * | 395 (193-xx) | 379 (60-508) |
| Duration of Exposure (Days)* | 99.5 (4-283) | 65.5 (1-302) |
| Prior Cranial Irradiation | 5 (7.8) | 4 (6.5) |

FIG. 4

| Tumor Type | Projected COG 5-year EFS | STS ≤1 yr EFS | OBS ≤1 yr EFS | STS >1 yr OS | OBS >1 yr OS | Hearing Loss STS | Hearing Loss OBS |
|---|---|---|---|---|---|---|---|
| Germ Cell | 75% | 14/16 (87.5%) | 13/16 (81.3%) | 15/16 (93.8%) | 16/16 (100%) | 0 | 3/15 (20%) |
| Hepatoblastoma | 60% | 2/2 | 4/5 | 2/2 | 5/5 | 1/2 | 4/5 |
| Medulloblastoma | 55% | 8/10 (80.0%) | 9/14 (64.3%) | 7/10 (70.0%) | 12/14 (85.7%) | 3/9 (33.3%) | 10/10 (100%) |
| Neuroblastoma | 45% | 8/14 (57.1%) | 6/12 (50.0%) | 11/14 (78.6%) | 9/12 (75.0%) | 4/10 (40%) | 6/9 (66.7%) |
| Osteosarcoma | 70% | 5/15 (33.3%) | 7/15 (46.7%) | 9/15 (60.0%) | 11/15 (73.3%) | 5/12 (41.7%) | 7/15 (46.7%) |
| PNET | | 1/2 | 0 | 1/2 | 0 | | |
| RTT | | 0/2 | 0 | 0/2 | 0 | | |
| Carcinoma, NOS | | 0/1 | 0 | 0/1 | 0 | | |
| Choroid Plexus Carcinoma | | 0 | 0/1 | 0 | 1/1 | | |
| Anaplastic Astrocytoma | | 0 | 1/1 | 0 | 1/1 | | |

FIG. 11

| Characteristic | Observation (%) | STS (%) |
|---|---|---|
| Eligible | 38 | 40 |
| Age at enrollment (yrs) | | |
| < 5 | 15 (39.5) | 16 (40.0) |
| ≥ 5 | 23 (60.5) | 24 (60.0) |
| Sex | | |
| Male | 25 (65.8) | 22 (55.0) |
| Female | 13 (34.2) | 18 (45.0) |
| Race | | |
| White | 24 (63.2) | 25 (62.5) |
| Black | 7 (18.4) | 4 (10.0) |
| Other/Unknown | 7 (18.4) | 11 (27.5) |
| Ethnicity | | |
| Non-Hispanic | 30 (78.9) | 28 (70.0) |
| Hispanic | 8 (21.1) | 12 (30.0) |

FIG. 12

| Characteristic | Observation (%) | STS (%) |
|---|---|---|
| Diagnosis | | |
| Germ Cell Tumor | 9 (23.7) | 9 (22.5) |
| Osteosarcoma | 10 (26.3) | 11 (27.5) |
| Medulloblastoma | 12 (31.6) | 9 (22.5) |
| Neuroblastoma | 1 (2.6) | 7 (17.5) |
| Hepatoblastoma | 4 (10.5) | 2 (5.0) |
| Other | 2 (5.3) | 2 (5.0) |
| Cum. CDDP dose (mg/m$^2$) | 392 (193-618) | 384 (92-484) |
| Duration of Exposure (Days) | 126 (32-283) | 68 (1-302) |
| Prior Cranial Irradiation | 5 (13.2) | 2 (5.0) |

FIG. 14

| Characteristic | Observation (%) | STS (%) |
|---|---|---|
| Diagnosis | | |
| Germ Cell Tumor | 7 (26.9) | 7 (33.3) |
| Osteosarcoma | 5 (19.2) | 4 (19.0) |
| Medulloblastoma | 2 (7.7) | 3 (14.3) |
| Neuroblastoma | 11 (42.3) | 6 (28.6) |
| Hepatoblastoma | 1 (3.8) | 0 |
| Other | 0 | 1 (4.8) |
| Cum. CDDP dose (mg/m$^2$) | 398 (242-1410) | 375 (60-508) |
| Duration of Exposure (Days) | 67.5 (4-239) | 49 (3-210) |
| Prior Cranial Irradiation | 0 | 2 (9.5) |

FIG. 15

| Characteristic | Observation (%) | STS (%) |
|---|---|---|
| Eligible | 26 | 21 |
| Age at enrollment (yrs) | | |
| < 5 | 7 (26.9) | 5 (23.8) |
| ≥ 5 | 19 (73.1) | 16 (76.2) |
| Sex | | |
| Male | 16 (61.5) | 13 (61.9) |
| Female | 10 (38.5) | 8 (38.1) |
| Race | | |
| White | 15 (57.7) | 18 (81.0) |
| Black | 3 (11.5) | 1 (4.8) |
| Other/Unknown | 8 (30.8) | 3 (14.3) |
| Ethnicity | | |
| Non-Hispanic | 16 (61.5) | 12 (57.1) |
| Hispanic | 10 (38.5) | 9 (42.9) |

FIG. 19

| Characteristic | Observation (%) | STS (%) |
|---|---|---|
| Eligible | 16 | 16 |
| Age at enrollment (yrs) | | |
| < 5 | 1 (6.3) | 0 |
| ≥ 5 | 15 (93.8) | 16 (100.0) |
| Sex | | |
| Male | 12 (75.0) | 9 (56.3) |
| Female | 4 (25.0) | 7 (43.8) |
| Race | | |
| White | 9 (56.3) | 9 (56.3) |
| Black | 2 (12.5) | 1 (6.3) |
| Other/Unknown | 5 (31.3) | 6 (37.5) |
| Ethnicity | | |
| Non-Hispanic | 10 (62.5) | 5 (31.3) |
| Hispanic | 6 (37.5) | 11 (68.8) |
| Extent of Disease | | |
| Localized | 9 (56.3) | 9 (56.3) |
| Disseminated | 7 (43.8) | 7 (43.8) |
| Unknown | 0 | 0 |
| Cum. CDDP dose (mg/m$^2$) | 393 (193-618) | 301 (60-508) |
| Prior Cranial Irradiation | 0 | 0 |

FIG. 21

| Characteristic | Observation (%) | SCE (%) |
|---|---|---|
| Eligible | 5 | 2 |
| Age at enrollment (yrs) | | |
| < 5 | 5 (100.0) | 1 (50.0) |
| ≥ 5 | 0 | 1 (50.0) |
| Sex | | |
| Male | 3 (60.0) | 1 (50.0) |
| Female | 2 (40.0) | 1 (50.0) |
| Race | | |
| White | 4 (80.0) | 1 (50.0) |
| Black | 1 (20.0) | 1 (50.0) |
| Other/Unknown | 0 | 0 |
| Ethnicity | | |
| Non-Hispanic | 4 (80.0) | 0 |
| Hispanic | 1 (20.0) | 2 (100.0) |
| Extent of Disease | | |
| Localized | 4 (80.0) | 2 (100.0) |
| Disseminated | 1 (20.0) | 0 |
| Unknown | 0 | 0 |
| Cum. CDDP dose (mg/m$^2$) | 421 (310-617) | 337 (279-394) |
| Prior Cranial Irradiation | 0 | 0 |

FIG. 23

| Characteristic | Observation (%) | STS (%) |
|---|---|---|
| Eligible | 14 | 12 |
| Age at enrollment (yrs) | | |
| < 5 | 6 (42.9) | 8 (66.7) |
| ≥ 5 | 8 (57.1) | 4 (33.3) |
| Sex | | |
| Male | 11 (78.6) | 8 (66.7) |
| Female | 3 (21.4) | 4 (33.3) |
| Race | | |
| White | 9 (64.3) | 8 (66.7) |
| Black | 2 (14.3) | 2 (16.7) |
| Other/Unknown | 3 (21.4) | 2 (16.7) |
| Ethnicity | | |
| Non-Hispanic | 11 (78.6) | 10 (83.3) |
| Hispanic | 3 (21.4) | 2 (16.7) |
| Extent of Disease | | |
| Localized | 12 (85.7) | 9 (75.0) |
| Disseminated | 2 (14.3) | 3 (25.0) |
| Unknown | 0 | 0 |
| Cum. CDDP dose (mg/m$^2$) | 364 (245-600) | 346 (92-441) |
| Prior Cranial Irradiation | 5 (35.7) | 3 (25.0) |

FIG. 25

| Characteristic | Observation (%) | STS (%) |
|---|---|---|
| Eligible | 12 | 14 |
| Age at enrollment (yrs) | | |
| < 5 | 7 (58.3) | 10 (71.4) |
| ≥ 5 | 5 (41.7) | 4 (28.6) |
| Sex | | |
| Male | 6 (50.0) | 7 (50.0) |
| Female | 6 (50.0) | 7 (50.0) |
| Race | | |
| White | 8 (66.7) | 12 (85.7) |
| Black | 1 (8.3) | 1 (7.1) |
| Other/Unknown | 3 (25.0) | 1 (7.1) |
| Ethnicity | | |
| Non-Hispanic | 7 (58.3) | 12 (85.7) |
| Hispanic | 5 (41.7) | 2 (14.3) |
| Extent of Disease | | |
| Localized | 1 (8.3) | 7 (50.0) |
| Disseminated | 11 (91.7) | 6 (42.9) |
| Unknown | 0 | 1 (7.1) |
| Cum. CDDP dose (mg/m$^2$) | 395 (278-1410) | 387 (198-421) |
| Prior Cranial Irradiation | 0 | 0 |

FIG. 27

| Characteristic | Observation (%) | SSS (%) |
|---|---|---|
| Eligible | 15 | 15 |
| Age at enrollment (yrs) | | |
| < 5 | 1 (6.7) | 1 (6.7) |
| ≥ 5 | 14 (93.3) | 14 (93.3) |
| Sex | | |
| Male | 8 (53.3) | 9 (60.0) |
| Female | 7 (46.7) | 6 (40.0) |
| Race | | |
| White | 8 (53.3) | 10 (66.7) |
| Black | 5 (33.3) | 1 (6.7) |
| Other/Unknown | 2 (13.3) | 4 (26.7) |
| Ethnicity | | |
| Non-Hispanic | 13 (86.7) | 11 (73.3) |
| Hispanic | 2 (13.3) | 4 (26.7) |
| Extent of Disease | | |
| Localized | 10 (66.7) | 11 (73.3) |
| Disseminated | 5 (33.3) | 4 (26.7) |
| Unknown | 0 | 0 |
| Cum. CDDP dose (mg/m$^2$) | 472 (242-489) | 472 (120-484) |
| Prior Cranial Irradiation | 0 | 1 (6.7) |

FIG. 30

| Characteristic | Observation (%) | STI (%) |
|---|---|---|
| Eligible | 22 | 22 |
| Age at enrollment (yrs) | | |
|  | 2 (1-5) | 2 (1-5) |
| Sex | | |
| Male | 12 (54.5) | 11 (50.0) |
| Female | 10 (45.5) | 11 (50.0) |
| Race | | |
| White | 13 (59.1) | 17 (77.3) |
| Black | 3 (13.6) | 3 (13.6) |
| Other/Unknown | 6 (27.3) | 2 (9.1) |
| Ethnicity | | |
| Non-Hispanic | 16 (72.7) | 20 (90.9) |
| Hispanic | 6 (27.3) | 2 (9.1) |

FIG. 31

| Characteristic | Observation (%) | STS (%) |
|---|---|---|
| Diagnosis | | |
| Germ Cell Tumor | 1 (4.5) | 0 |
| Osteosarcoma | 1 (4.5) | 1 (4.5) |
| Medulloblastoma | 6 (27.3) | 8 (36.4) |
| Neuroblastoma | 7 (31.8) | 10 (45.5) |
| Hepatoblastoma | 5 (22.7) | 1 (4.5) |
| Other | 2 (9.1) | 2 (9.1) |
| Extent of Disease | | |
| Localized | 15 (68.2) | 16 (72.2) |
| Disseminated | 7 (31.8) | 5 (22.7) |
| Unknown | 0 | 1 (4.5) |
| Cum. CDDP dose (mg/m$^2$) | 391 (245-618) | 287 (92-426) |
| Duration of Exposure (Days) | 93.5 (46-203) | 57 (1-127) |
| Prior Cranial Irradiation | 0 | 0 |

FIG. 33

| Characteristic | Observation (%) | STS (%) |
|---|---|---|
| Eligible | 42 | 40 |
| Age at enrollment (yrs) | | |
|  | 13 (5-18) | 14 (6-18) |
| Sex | | |
| Male | 29 (69.0) | 24 (60.0) |
| Female | 13 (31.0) | 16 (40.0) |
| Race | | |
| White | 26 (61.9) | 26 (65.0) |
| Black | 7 (16.7) | 2 (5.0) |
| Other/Unknown | 9 (21.4) | 12 (30.0) |
| Ethnicity | | |
| Non-Hispanic | 30 (71.4) | 21 (52.5) |
| Hispanic | 12 (28.6) | 19 (47.5) |

FIG. 34

| Characteristic | Observation (%) | STS (%) |
|---|---|---|
| Diagnosis | | |
| Germ Cell Tumor | 15 (35.7) | 16 (40.0) |
| Osteosarcoma | 14 (33.3) | 14 (35.0) |
| Medulloblastoma | 8 (19.0) | 4 (10.0) |
| Neuroblastoma | 5 (11.9) | 4 (10.0) |
| Hepatoblastoma | 0 | 1 (2.5) |
| Other | 0 | 1 (2.5) |
| Extent of Disease | | |
| Localized | 23 (54.8) | 24 (60.0) |
| Disseminated | 19 (45.2) | 16 (40.0) |
| Unknown | 0 | 0 |
| Cum. CDDP dose (mg/m$^2$) | 397 (193-1410) | 394 (60-508) |
| Duration of Exposure (Days) | 110 (4-283) | 73 (3-302) |
| Prior Cranial Irradiation | 5 (11.9) | 4 (10.0) |

- Cisplatin over 6 hrs i.v. at a dose of $80mg/m^2$
- STS over 15 mins i.v. 6 hrs after stopping Cisplatin at $20g/m^2$
- The trial opened to recruitment in 2007 and closed in December 2014
- 52 centres participated in 11 countries worldwide:
  UK, France, Belgium, Japan, Italy, Spain, Australia, New Zealand, Ireland, Switzerland, USA

FIG. 38

Patient Characteristics

|  | Cis (N=52) | Cis+STS (N=57) |
|---|---|---|
| Age (months) | Median 13<br>Range 3.0 – 70 | Median 13<br>Range 1.2 – 99 |
| AFP (ng/mL) | Median 73,760<br>Range<br>187 – 2,175,690 | Median 154,638<br>Range<br>273 – 4,536,500 |
| Sex | M: 29   56%<br>F: 23   44% | M: 30   53%<br>F: 27   47% |
| PRETEXT   I/II<br>III | 31   60%<br>21   40% | 41   72%<br>16   28% |

FIG. 39

Adverse Events

| Adverse event | Grade | Cis | | Cis+STS | |
|---|---|---|---|---|---|
| | | #pts | % | #pts | % |
| Febrile neutropenia | 3 | 7 | 13.5 | 5 | 8.8 |
| | 4 | - | - | - | - |
| Infection | 3 | 5 | 9.6 | 6 | 10.5 |
| | 4 | - | - | - | - |
| Hypomagnesemia | 3 | 1 | 1.9 | 1 | 1.8 |
| | 4 | - | - | - | - |
| Hypernatremia | 3 | - | - | 1 | 1.8 |
| | 4 | - | - | - | - |
| Vomiting | 3 | 1 | 1.9 | 3 | 5.3 |
| | 4 | - | - | - | - |
| Nausea | 3 | 3 | 5.8 | 2 | 3.5 |
| | 4 | - | - | - | - |

3yr-EFS Cis 78.8%, Cis+STS 82.1%

3yr-OS Cis 92.3%, Cis+STS 98.2%

METHOD FOR REDUCING OTOTOXICITY IN PEDIATRIC PATIENTS RECEIVING PLATINUM-BASED CHEMOTHERAPY

CROSS REFERENCE TO RELATED APPLICATIONS

This application is a continuation of U.S. application Ser. No. 15/826,243, filed Nov. 29, 2017, the entire contents of which are hereby incorporated herein by reference.

GOVERNMENT INTEREST

This invention was made with support by the United States government under R01-CA137488 and R01-NS044687 awarded by the National Institutes of Health. The United States government has certain rights in the invention.

TECHNICAL FIELD

Described herein is a method for eliminating or reducing ototoxicity in patients receiving a platinum based chemotherapeutic. In particular, are methods of reducing ototoxicity in a pediatric patient.

BACKGROUND

Platinum based therapeutics are highly important components of treatment regimens used in a variety of pediatric malignancies including neuroblastoma, hepatoblastoma, medulloblastoma, osteosarcoma, malignant germ cell tumors and nasopharyngeal carcinomas. Unfortunately, at commonly used doses and schedules, platinum based therapeutics, such as cisplatin and carboplatin, frequently cause hearing loss that is progressive, bilateral, irreversible, and often accompanied by tinnitus. Platinum chemotherapeutic based hearing loss can affect all hearing frequencies owing to the death of cochlear outer hair cells.

These toxicities can be dose-limiting and is often clinically significant, especially in young children who are critically dependent upon normal hearing for cognitive, psychosocial and speech development. Approximately 40% of children develop cisplatin-induced hearing loss with nearly 100% incidence for certain vulnerable groups. The effects of even mild hearing loss in pediatrics is substantial with, inter alia, reduced language acquisition, learning, academic performance, social and emotional development, and life quality. Thus, there is a need for safe and effective methods for treating pediatric patients to reduce ototoxicity and hearing loss in these patients that do not compromise the efficacy of the platinum-based therapeutic.

SUMMARY

Described herein are methods for reducing ototoxicity in patients having received a platinum based chemotherapeutic. In particular, are methods for reducing ototoxicity in pediatric patients. The methods include administering an effective amount of sodium thiosulfate (STS) to the patient following administration of the platinum based chemotherapeutic. As described herein, the administration of STS was found to not adversely affect the efficacy of the platinum based chemotherapeutic and decreased the incidence and severity of ototoxicity in pediatric patients.

One embodiment is a method of reducing ototoxicity in a patient having a cancer and receiving a platinum based chemotherapeutic comprising administering an effective amount of sodium thiosulfate to the patient.

Another embodiment is a method of prophylactically treating a patient having a cancer and receiving a platinum based chemotherapeutic to reduce a likelihood of the patient incurring ototoxicity comprising administering an effective amount of sodium thiosulfate to the patient.

Another embodiment is a method of reducing long term ototoxicity in a patient having a cancer and receiving a platinum based chemotherapeutic comprising administering an effective amount of sodium thiosulfate to the patient.

Another embodiment is a method of reducing a concentration of cisplatin in an aural cavity of a patient having a cancer and receiving a platinum based chemotherapeutic comprising administering an effective amount of sodium thiosulfate to the patient, wherein substantially no cisplatin is detectable in the aural cavity and wherein the patient administered the sodium thiosulfate is less susceptible to incurring ototoxicity from the platinum based chemotherapeutic.

Another embodiment is a method of inhibiting ototoxic effects associated with an administration of platinum based chemotherapeutic compounds in a patient comprising administering an effective amount of sodium thiosulfate to the patient.

In some embodiments described herein, the patient carries has single nucleotide polymorphism in a gene ACYP2 at locus rs1872328. In some embodiments, the patient administered sodium thiosulfate is about 20% to about 75% less likely to experience ototoxicity than a patient not administered sodium thiosulfate. In some embodiments, the patient administered sodium thiosulfate is about 50% less likely to experience ototoxicity than a patient not administered sodium thiosulfate. In some embodiments ototoxicity comprises hearing loss, dysequilibrium, tinnitus, or hearing sensitivity or combinations thereof.

In some embodiments described herein, the platinum based chemotherapeutic is selected from cisplatin, carboplatin, oxaliplatin, nedaplatin, triplatin tetranitrate, phenanthriplatin, picoplatin, and satraplatin. In some embodiments, the platinum based chemotherapeutic is cisplatin.

In some embodiments, the cancer being treated is localized or disseminated. In some embodiments, the cancer being treated is localized. In some embodiments, the cancer being treated is selected from a germ cell tumor, hepatoblastoma, medulloblastoma, neuroblastoma, and osteosarcoma. In some embodiments, the cancer being treated is hepatoblastoma. In some embodiments, the cancer being treated is a standard risk cancer, intermediate risk cancer, or high risk cancer. In some embodiments, the cancer being treated is a standard risk cancer or an intermediate risk cancer. In some embodiments, the cancer being treated is standard risk or intermediate risk hepatoblastoma.

In some embodiments, the sodium thiosulfate is administered prior to, concurrently with, or after the administration of the platinum based chemotherapeutic. In some embodiments, the sodium thiosulfate is administered about 0.5 hours to about 10 hours after the administration of the platinum based chemotherapeutic. In some embodiments, the sodium thiosulfate is administered intravenously. In some embodiments, the effective amount of sodium thiosulfate is from about 5 g/m$^2$ to about 25 g/m$^2$ per cycle of the platinum based chemotherapeutic. In some embodiments, the patient is being treated with a dose of about 1 mg/kg to about 5 mg/kg or about 10 mg/m$^2$ to about 300 mg/m$^2$ per cycle of the platinum based chemotherapeutic.

In some embodiments described herein, ototoxicity is determined by one or more criteria comprising: a tinnitus functional index, Brock grading, American Speech-Language-Hearing Association criteria, or International Society of Pediatric Oncology Boston Ototoxicity Scale. In some embodiments ototoxicity is determined by measuring a hearing loss at one or more frequencies comprising 500 Hz, 1,000 Hz, 2,000 Hz, 4,000 Hz, or 8,000 Hz or a combination of frequencies thereof, wherein a change in hearing is computed relative to baseline measures prior to the patient receiving a platinum based chemotherapeutic or sodium thiosulfate or both.

In some embodiments described herein, ototoxicity is determined by one or more criteria comprising: a). a reduction in hearing measured by a 20 dB loss at a single frequency; b). a reduction in hearing measured by a 10 dB loss at two consecutive frequencies; c). loss of response at three consecutive test frequencies where responses were previously obtained; d). a reduction in bilateral high-frequency hearing characterized by: i). a <40 dB hearing loss at all frequencies, which indicates a grade 0 or minimal hearing loss; ii). a ≥40 dB hearing loss at 8,000 Hz only, which indicates a grade 1 or mild hearing loss; iii). a ≥40 dB hearing loss at 4,000 Hz and above, which indicates a grade 2 or moderate hearing loss; iv). a ≥40 dB hearing loss at 2,000 Hz and above, which indicates a grade 3 or marked hearing loss; v). a ≥40 dB hearing loss at 1,000 Hz and above, which indicates a grade 4 or severe hearing loss; or e). a reduction in hearing characterized by: i). a ≤20 dB hearing loss at all frequencies, which indicates a grade 0 hearing loss; ii). a >20 dB HL above 4,000 Hz, which indicates a grade 1 hearing loss; iii). a >20 dB HL at 4,000 Hz and above, which indicates a grade 2 hearing loss; iv). a >20 dB HL at 2,000 Hz or 3,000 Hz, which indicates a grade 3 hearing loss; v). a >40 dB HL at 2,000 Hz and above, which indicates a grade 1 hearing loss, or f). an improvement in a tinnitus functional index; and wherein a change in hearing is computed relative to baseline measures prior to the patient receiving a platinum based chemotherapeutic or sodium thiosulfate or both. In some embodiments, the pediatric patient administered sodium thiosulfate has a reduction in ototoxicity assessed by criterion d) described above compared to a pediatric patient not administered sodium thiosulfate.

In some embodiments described herein, the administration of sodium thiosulfate to a patient does not lead to increased serum creatinine or a reduction in glomerular filtration rate compared to a patient not administered sodium thiosulfate. In some embodiments, the administration of sodium thiosulfate to a patient does not affect relapse free survival or overall survival compared to a patient not administered sodium thiosulfate. In some embodiments, the administration of sodium thiosulfate to a patient does not lead to increased incidence of one or more adverse events comprising febrile neutropenia, infection, hypomagnesemia, hypernatremia, vomiting, or nausea.

In some embodiments described herein, ototoxicity is measured at a time of at least 4 weeks following the administration of the platinum based chemotherapeutic and sodium thiosulfate to a patient.

In some embodiments described herein, the patient is a pediatric patient. In some embodiments described herein, the pediatric patient is 1 week of age to 18 years of age. In some embodiments, the pediatric patient is about 12 years of age or less. In some embodiments, the pediatric patient is about 5 years of age or less. In some embodiments, the pediatric patient is about 2 years of age or less. In some embodiments, the pediatric patient is about 1 year of age or less.

Another embodiment is a dosing regimen for treating hepatoblastoma in a pediatric patient comprising: a). administering a dose of about 1 mg/kg to about 5 mg/kg or about 10 mg/m$^2$ to about 300 mg/m$^2$ per cycle of cisplatin; b). administering about 5 g/m$^2$ to about 25 g/m$^2$ of sodium thiosulfate per cycle of the cisplatin, wherein the sodium thiosulfate is administered from about 2 hours to about 6 hours after the administration of the cisplatin; and wherein the dosing regimen achieves a reduction in ototoxicity when dosed to a pediatric patient compared to a dosing regimen not including the sodium thiosulfate, which is dosed to a pediatric patient, wherein ototoxicity is determined by one or more criteria selected from: a). a reduction in hearing measured by a 20 dB loss at a single frequency; b). a reduction in hearing measured by a 10 dB loss at two consecutive frequencies; c). loss of response at three consecutive test frequencies where responses were previously obtained; d). a reduction in bilateral high-frequency hearing characterized by the criteria: i). a <40 dB hearing loss at all frequencies, which indicates a grade 0 or minimal hearing loss; ii). a ≥40 dB hearing loss at 8,000 Hz only, which indicates a grade 1 or mild hearing loss; iii). a ≥40 dB hearing loss at 4,000 Hz and above, which indicates a grade 2 or moderate hearing loss; iv). a ≥40 dB hearing loss at 2,000 Hz and above, which indicates a grade 3 or marked hearing loss; v). a ≥40 dB hearing loss at 1,000 Hz and above, which indicates a grade 4 or severe hearing loss; or e). a reduction in hearing characterized by the criteria: i). a ≤20 dB hearing loss at all frequencies, which indicates a grade 0 hearing loss; ii). a >20 dB HL above 4,000 Hz, which indicates a grade 1 hearing loss; iii). a >20 dB HL at 4,000 Hz and above, which indicates a grade 2 hearing loss; iv). a >20 dB HL at 2,000 Hz or 3,000 Hz, which indicates a grade 3 hearing loss; v). a >40 dB HL at 2,000 Hz and above, which indicates a grade 1 hearing loss; wherein a change in hearing is computed relative to baseline measures prior to the patient receiving a platinum based chemotherapeutic or sodium thiosulfate or both.

Another embodiment is method of reducing ototoxicity in a pediatric patient of about 12 years of age and under having a standard risk or an intermediate risk hepatoblastoma and receiving a dose of about 1 mg/kg to about 5 mg/kg or about 10 mg/m$^2$ to about 300 mg/m$^2$ per cycle of cisplatin, the method comprising administering about 5 g/m$^2$ to about 25 g/m$^2$ of sodium thiosulfate per cycle of the cisplatin about six hours after the administration of the cisplatin, wherein ototoxicity is determined by one or more criteria selected from: a). a reduction in hearing measured by a 20 dB loss at a single frequency; b). a reduction in hearing measured by a 10 dB loss at two consecutive frequencies; c). loss of response at three consecutive test frequencies where responses were previously obtained; d). a reduction in bilateral high-frequency hearing characterized by the criteria: i). a <40 dB hearing loss at all frequencies, which indicates a grade 0 or minimal hearing loss; ii). a ≥40 dB hearing loss at 8,000 Hz only, which indicates a grade 1 or mild hearing loss; iii). a ≥40 dB hearing loss at 4,000 Hz and above, which indicates a grade 2 or moderate hearing loss; iv). a ≥40 dB hearing loss at 2,000 Hz and above, which indicates a grade 3 or marked hearing loss; v). a ≥40 dB hearing loss at 1,000 Hz and above, which indicates a grade 4 or severe hearing loss; or e). a reduction in hearing characterized by the criteria: i). a ≤20 dB hearing loss at all frequencies, which indicates a grade 0 hearing loss; ii). a >20 dB HL above 4,000 Hz, which indicates a grade 1 hearing loss; iii). a >20 dB HL at 4,000 Hz and above, which indicates a grade 2 hearing loss; iv). a >20 dB HL at 2,000 Hz or 3,000 Hz, which indicates a grade 3 hearing loss; v). a >40 dB HL at 2,000 Hz and above, which indicates a grade 1 hearing loss; wherein a change in hearing is computed relative to baseline measures prior to the patient receiving a platinum based chemotherapeutic or sodium thiosulfate or both; and wherein the administration of sodium thiosulfate does not substantively affect relapse free survival or overall survival compared to a pediatric patient not administered sodium thiosulfate; and wherein the administration of sodium thiosulfate does not lead to substantively increased incidence of one or more adverse events comprising febrile neutropenia, infection, hypomagnesemia, hypernatremia, vomiting, or nausea.

BRIEF DESCRIPTION OF THE DRAWINGS

FIG. 2 is a table providing the demographics of patients enrolled in the study of Example 1.

FIG. 3 is a table providing the categorization of patient tumor types both in the control (observation) arm and the STS arm of the study of Example 1.

FIG. 4 is a table providing additional categorization information for patient tumor types both in the control (observation) arm and the STS arm and associated event free survival (EFS) and overall survival (OS) of the study of Example 1.

FIG. 11 is a table providing the demographics of patients with localized tumors enrolled in the study of Example 1.

FIG. 12 is a table providing the demographics of patients with localized tumors enrolled in the study of Example 1.

FIG. 14 is a table providing the characteristics of the tumors of patients with disseminated disease enrolled in the study of Example 1.

FIG. 15 is a table providing the demographics of the patients with disseminated disease enrolled in the study of Example 1.

FIG. 19 is a table providing the demographics of patients with germ cell tumors enrolled in the study of Example 1.

FIG. 21 is a table providing the demographics of patients with hepatoblastoma tumors enrolled in the study of Example 1.

FIG. 23 is a table providing the demographics of patients with medulloblastoma tumors enrolled in the study of Example 1.

FIG. 25 is a table providing the demographics of patients with neuroblastoma tumors enrolled in the study of Example 1.

FIG. 27 is a table providing the demographics of patients with osteosarcoma tumors enrolled in the study of Example 1.

FIG. 30 is a table providing the demographics of patients under the age of 5 enrolled in the study of Example 1.

FIG. 31 is a table providing the characteristics of the tumors for patients under the age of 5 enrolled in the study of Example 1.

FIG. 33 is a table providing the demographics of patients greater than or equal to the age of 5 enrolled in the study of Example 1.

FIG. 34 is a table providing the characteristics of the tumors for patients greater than or equal to the age of 5 enrolled in the study of Example 1.

FIG. 38 is a table providing the demographics of patients enrolled in the study of Example 2.

FIG. 39 is a table that shows the incidence rate of adverse events including grade 3 or 4 febrile neutropenia, invention, hypomagnesemia, hypernatremia, vomiting, and nausea both for the control arm (cisplatin treated only) and the cisplatin +STS arm for the study of Example 2.

DETAILED DESCRIPTION

Figure 1:
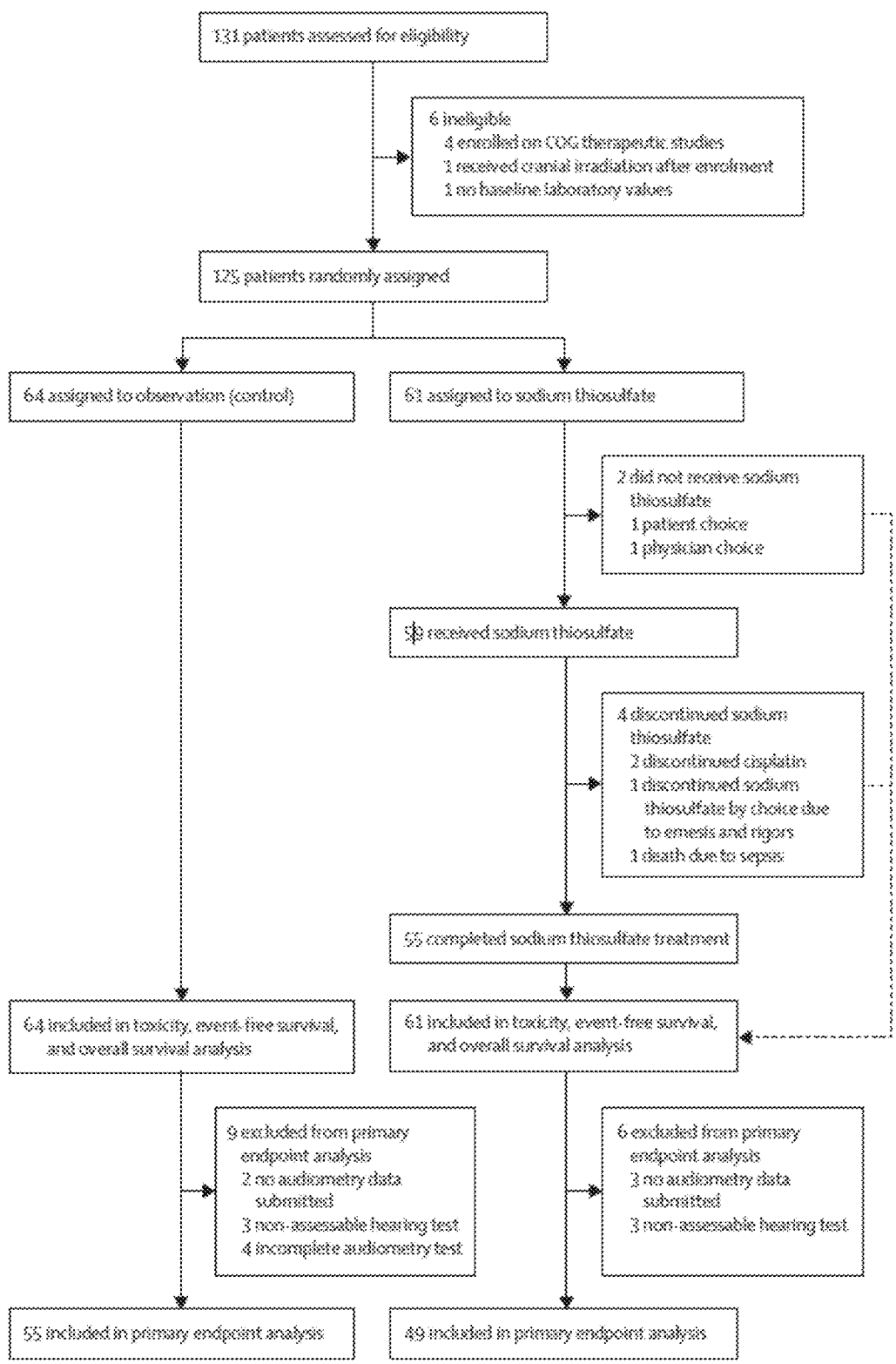
FIG. 1 is a flow diagram of patient eligibility and testing arms, either control or STS treated and the number of patients included at primary endpoint analysis for the study of Example 1.
Figure 5A:
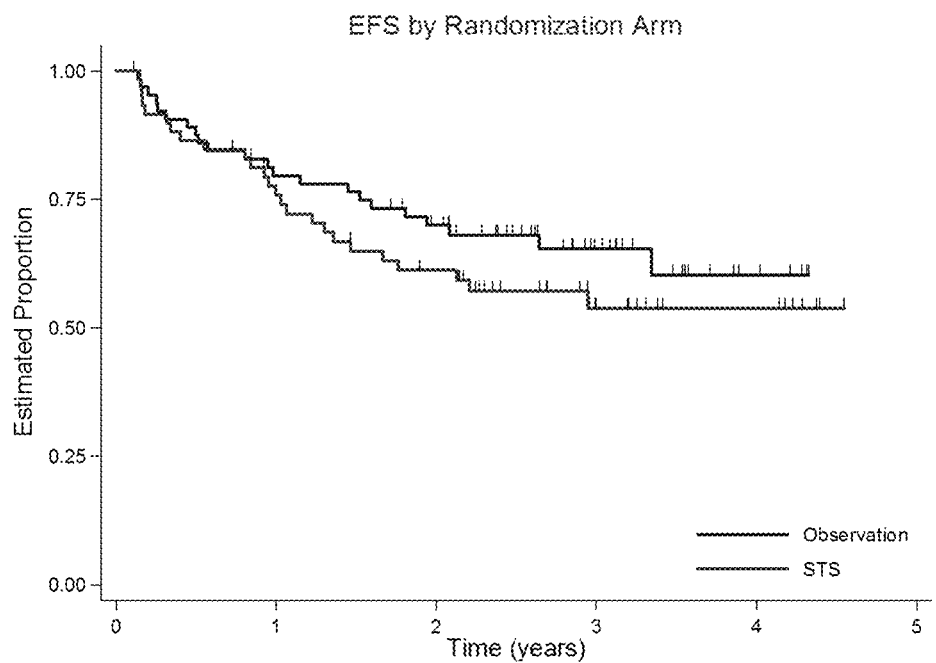
FIG. 5A is a Kaplan-Meier curve showing event free survival and overall survival for all 126 patients for the study of Example 1; the mean follow-up was 2.9 years.
Figure 5B:
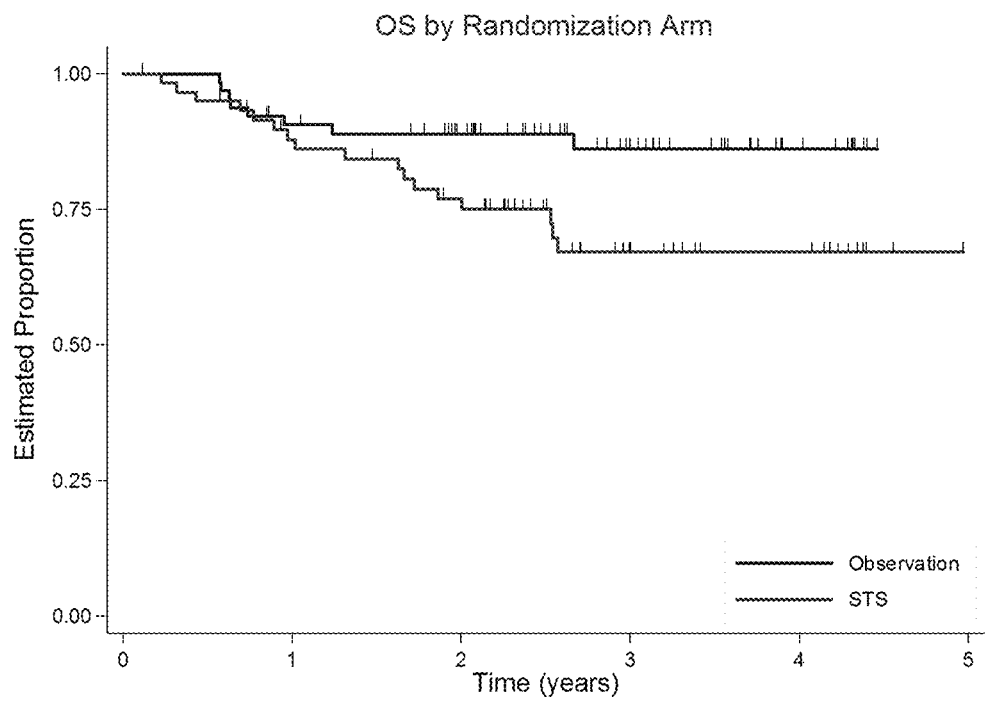
FIG. 5B is a Kaplan-Meier curve showing event free survival and overall survival for all 126 patients for the study of Example 1; the mean follow-up was 2.9 years.
Figure 6:
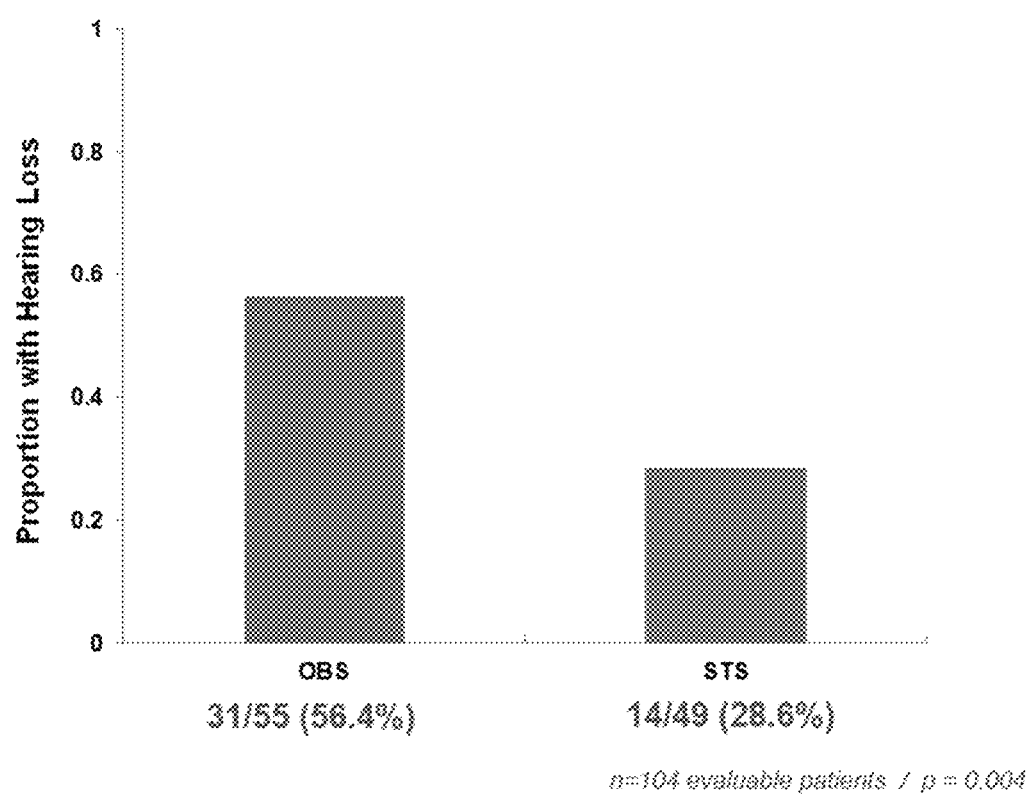
FIG. 6 is a bar graph showing hearing loss for either the observation (control) arm or the STS treatment arm for the study of Example 1.
Figure 7:
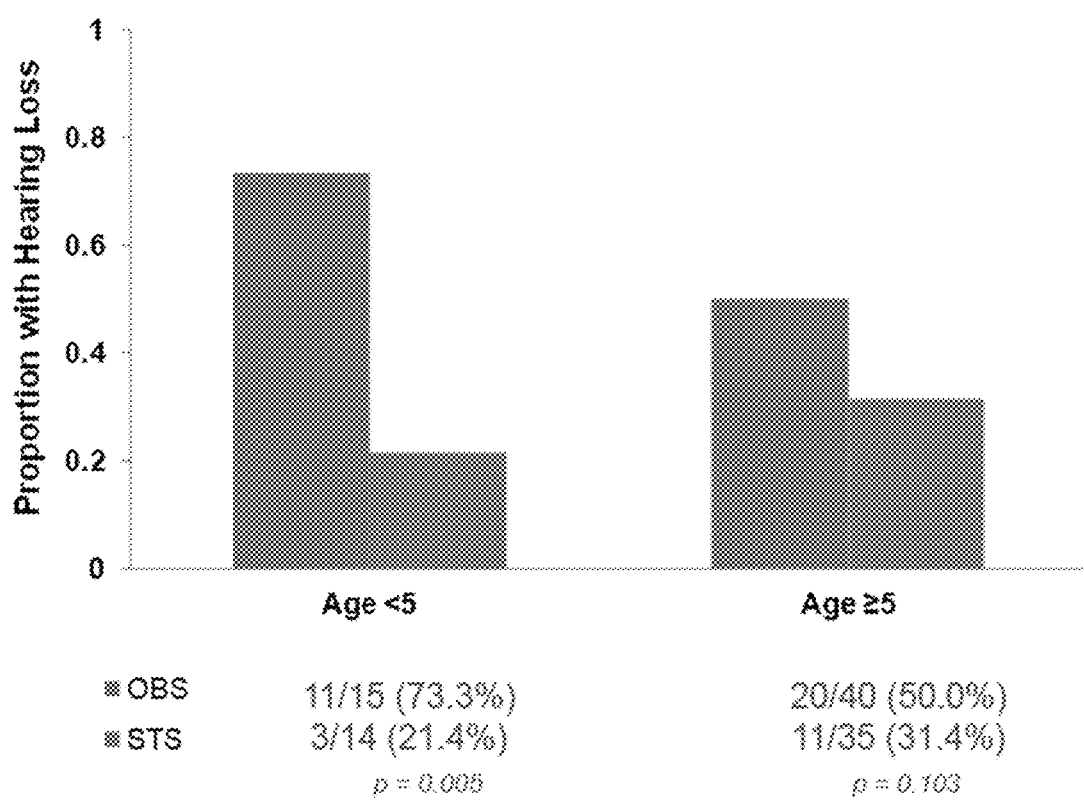
FIG. 7 is a bar graph showing hearing loss for either the observation (control) arm or the STS treatment arm with patients segmented by age either <5 or >5 years of age for the study of Example 1.
Figure 8:
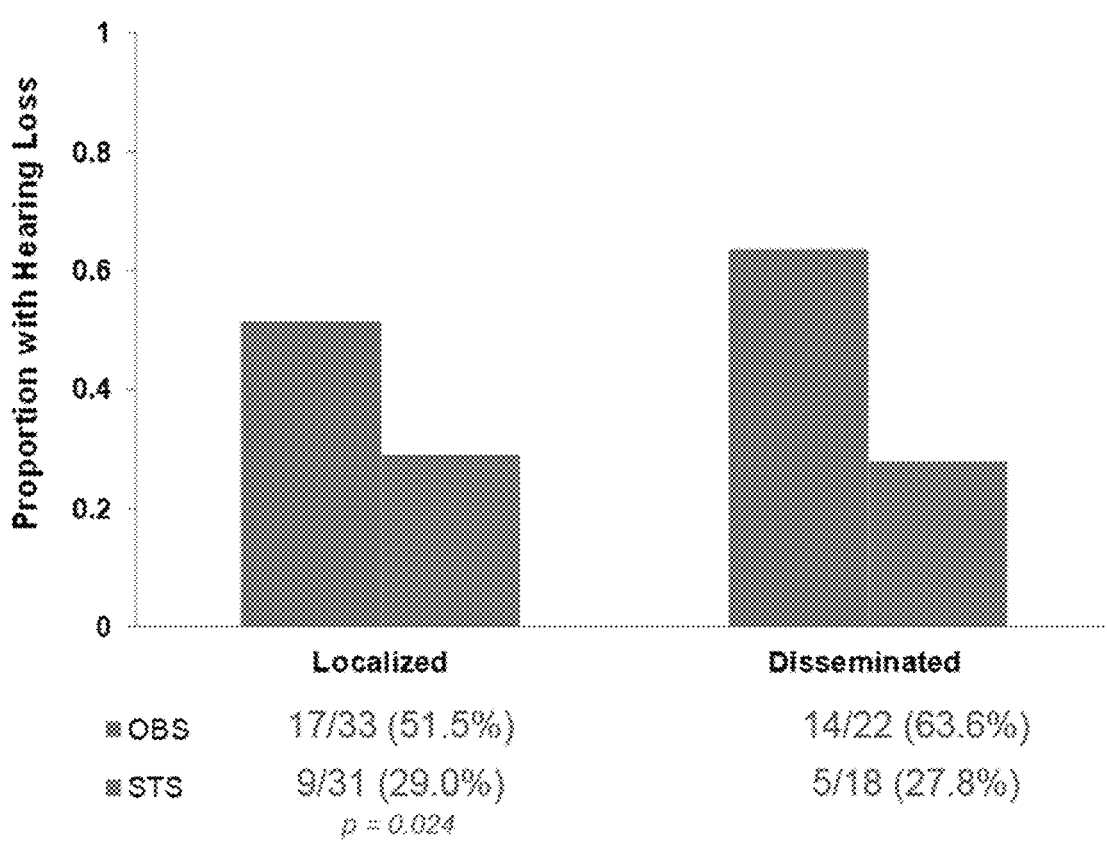
FIG. 8 is a bar graph showing hearing loss for either the observation (control) arm or the STS treatment arm with patients segmented by either localized or disseminated tumor for the study of Example 1.
Figure 9:
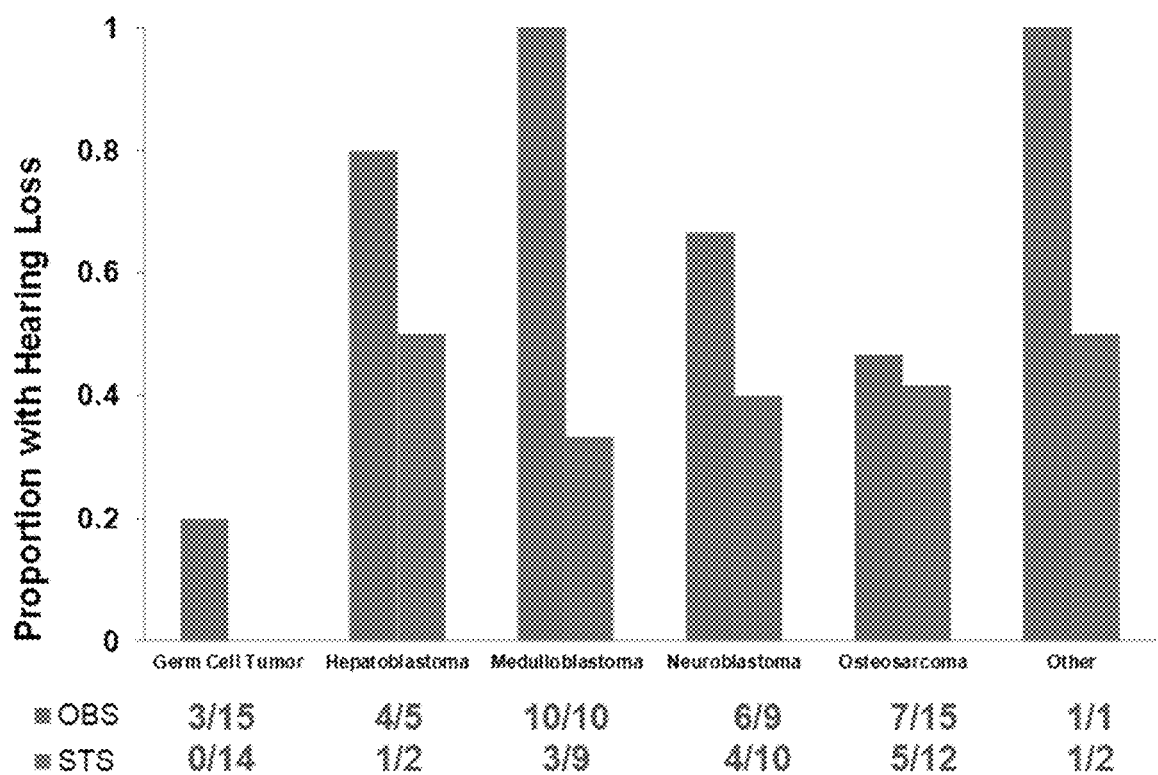
FIG. 9 is a bar graph showing hearing loss for either the observation (control) arm or the STS treatment arm with patients segmented by tumor type for the study of Example 1.
Figure 10:
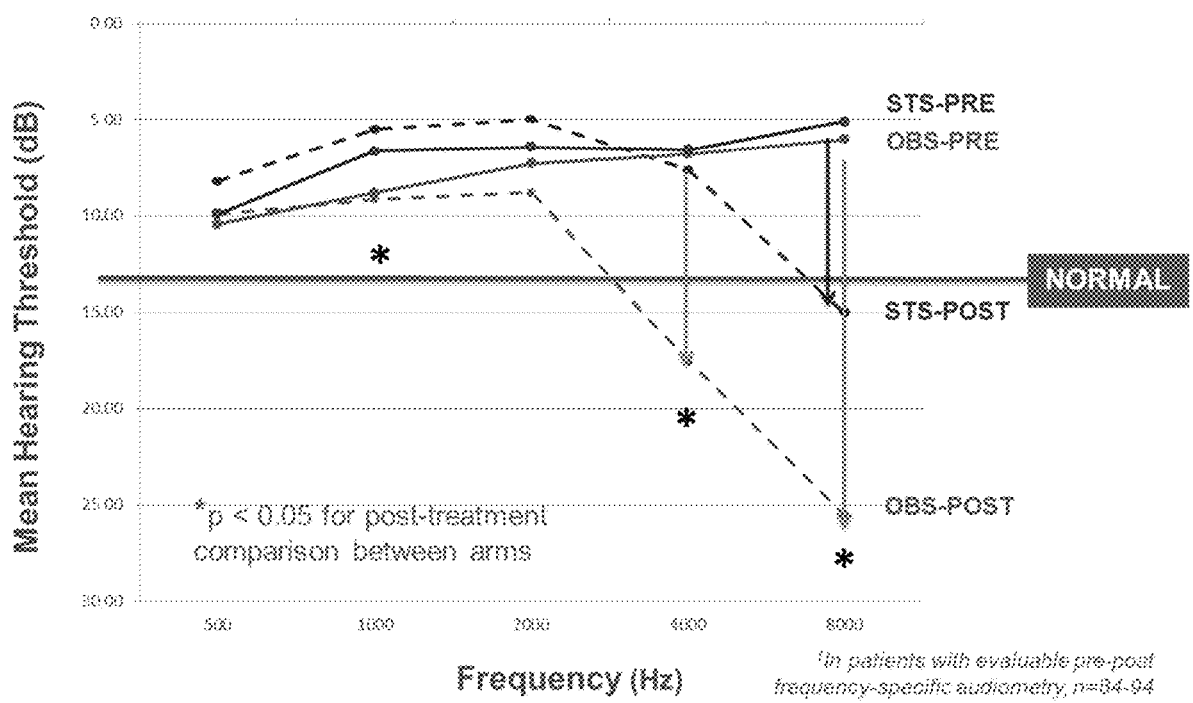
FIG. 10 is a graph showing the mean hearing threshold in dB for either observation (control) arm or the STS treatment arm showing hearing threshold pre-treatment and post-treatment for the study of Example 1.
Figure 13A:
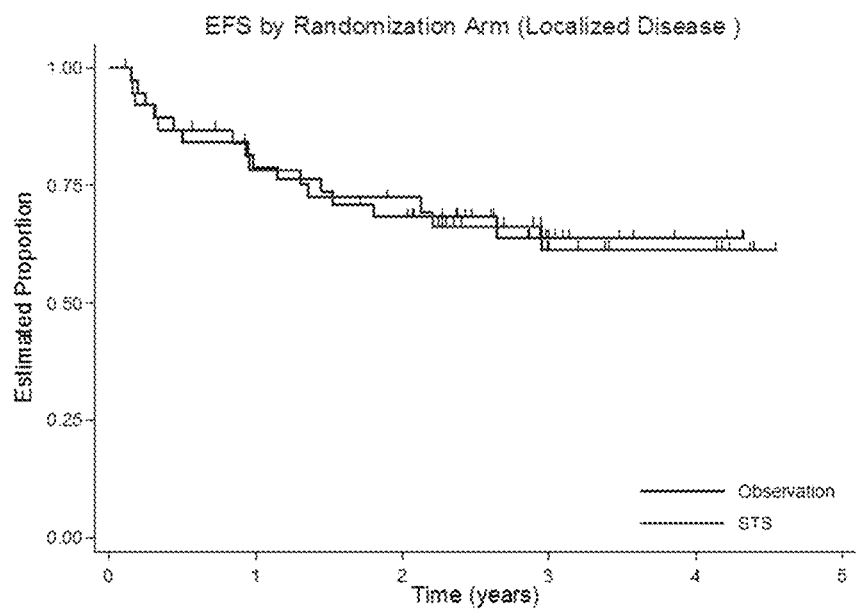
FIG. 13A is a Kaplan-Meier curve showing event free survival and overall survival segmented by patients having a localized tumor only for the study of Example 1.
Figure 13B:
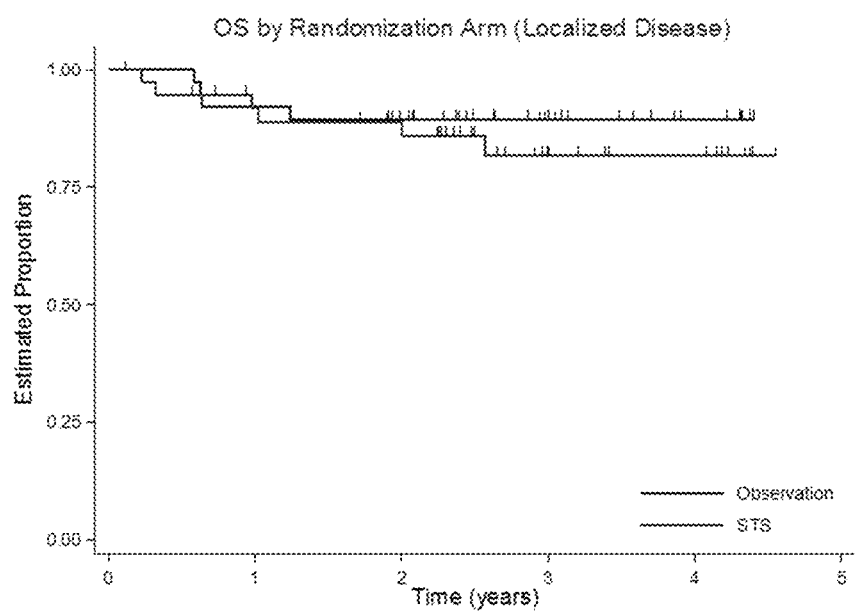
FIG. 13B is a Kaplan-Meier curve showing event free survival and overall survival segmented by patients having a localized tumor only for the study of Example 1.
Figure 16A:
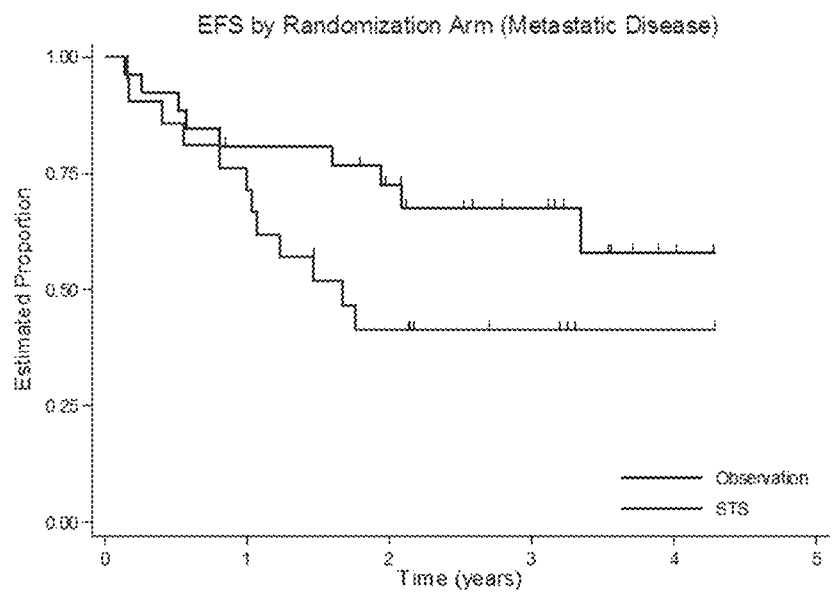
FIG. 16A is a Kaplan-Meier curve showing event free survival segmented by patients having a disseminated tumor only for the study of Example 1.
Figure 16B:
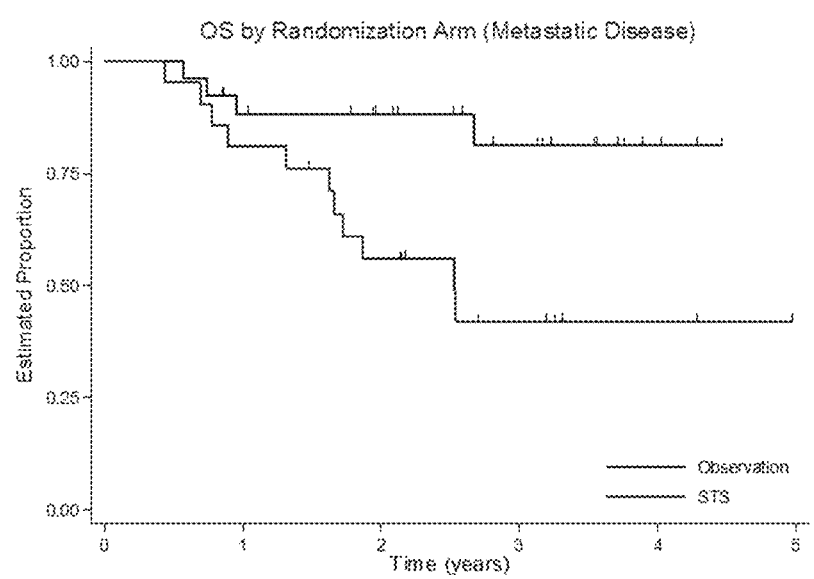
FIG. 16B is a Kaplan-Meier curve showing event overall survival segmented by patients having a disseminated tumor only for the study of Example 1.
Figure 17:
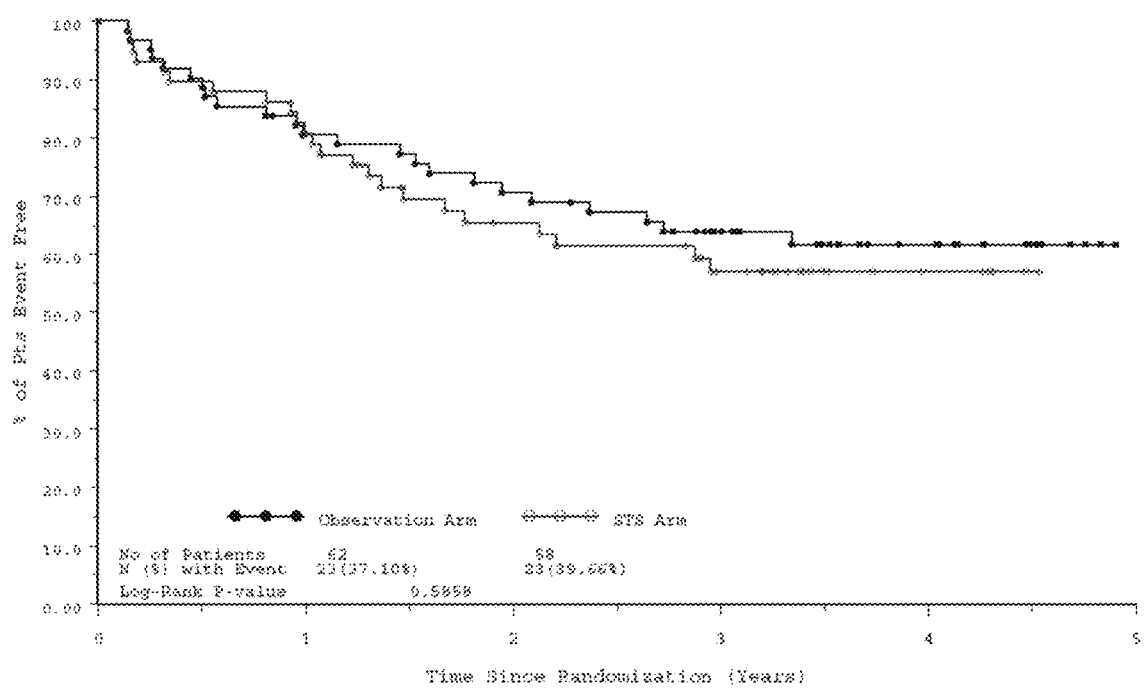
FIG. 17 is a Kaplan-Meier curve showing post-hoc analysis of event free survival excluding the group of other tumors for all patients for the study of Example 1.
Figure 18:
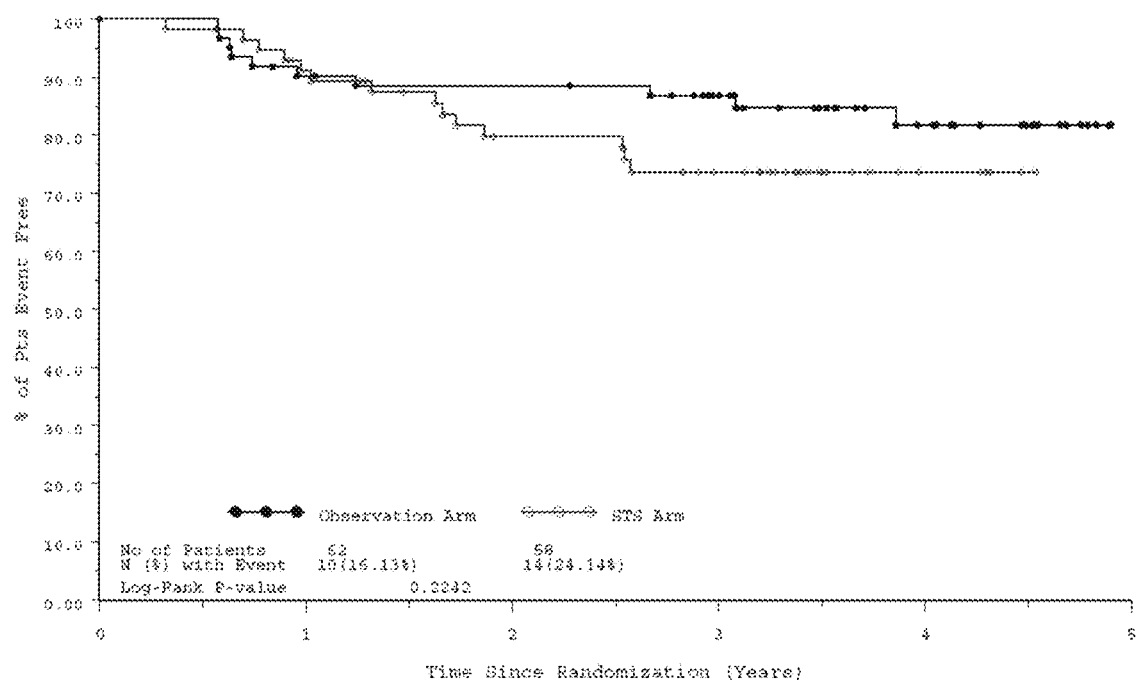
FIG. 18 is a Kaplan-Meier curve showing post-hoc analysis of overall survival excluding the group of other tumors for all patients for the study of Example 1.
Figure 20A:
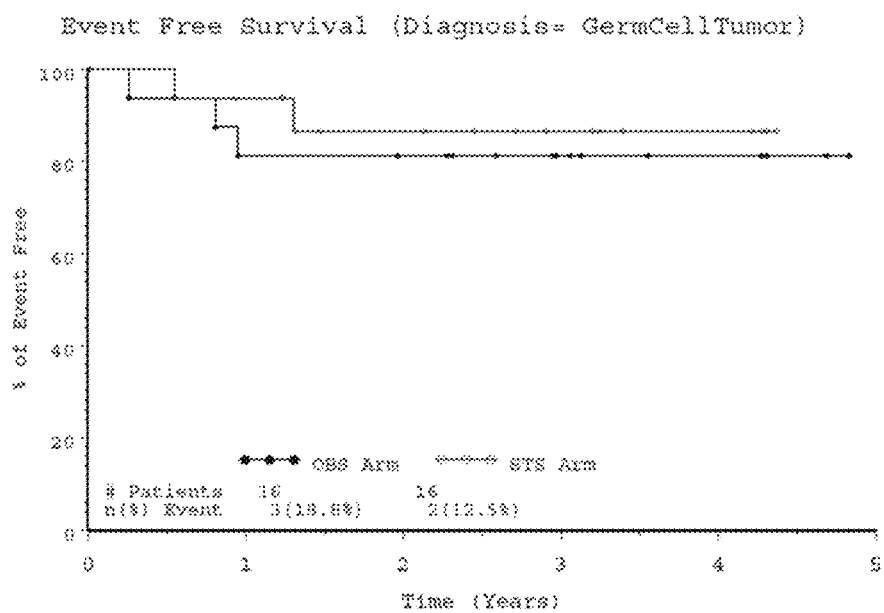
FIG. 20A is a Kaplan-Meier curve showing analysis of event free survival of patients having germ-cell tumors for the study of Example 1.
Figure 20B:
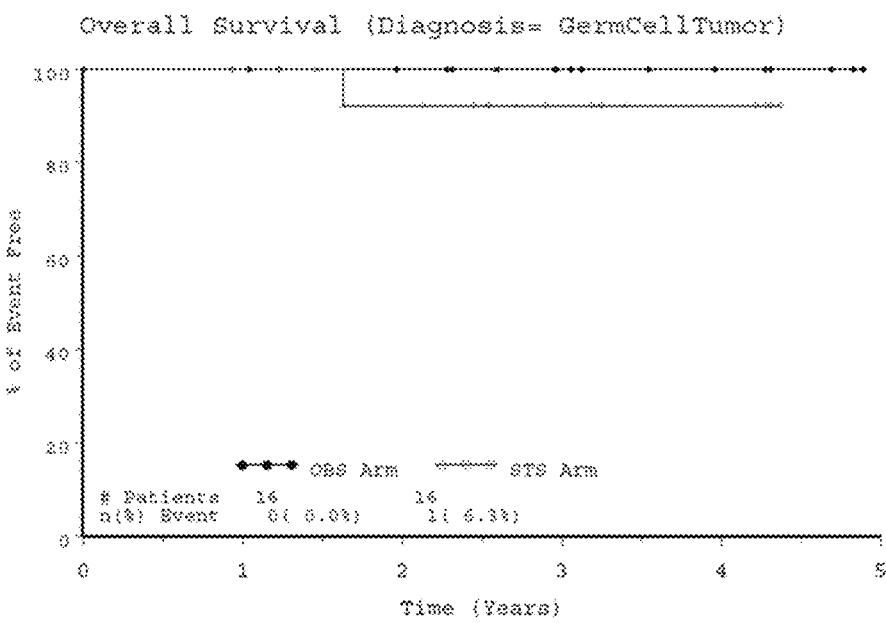
FIG. 20B is a Kaplan-Meier curve showing analysis of overall survival of patients having germ-cell tumors for the study of Example 1.
Figure 22A:
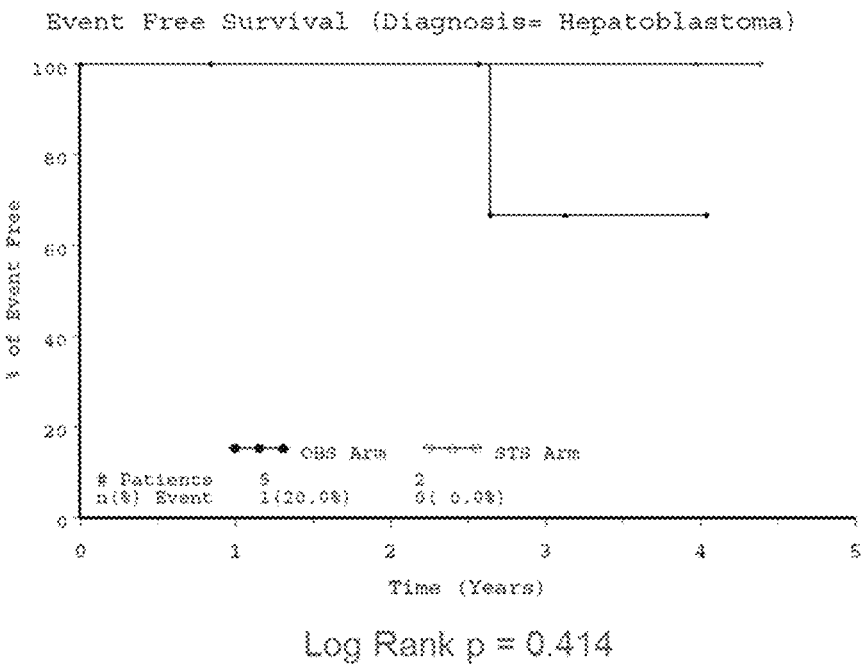
FIG. 22A is a Kaplan-Meier curve showing analysis of event free survival of patients having hepatoblastoma tumors for the study of Example 1.
Figure 22B:
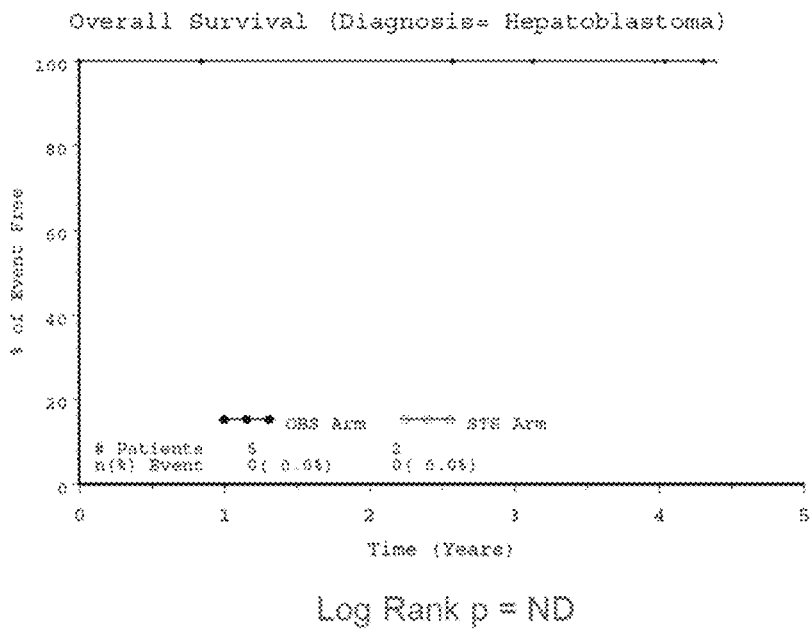
FIG. 22B is a Kaplan-Meier curve showing analysis of overall survival of patients having hepatoblastoma tumors for the study of Example 1.
Figure 24A:
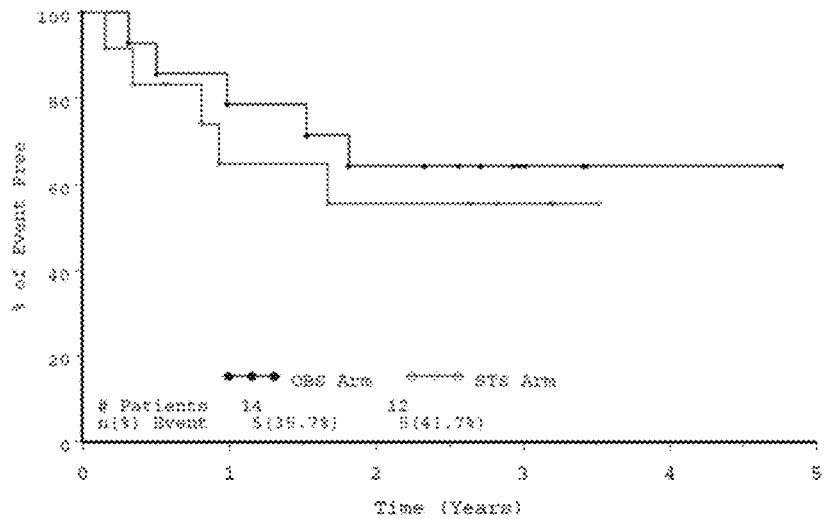
FIG. 24A is a Kaplan-Meier curve showing analysis of event free survival of patients having medulloblastoma tumors for the study of Example 1.
Figure 24B:
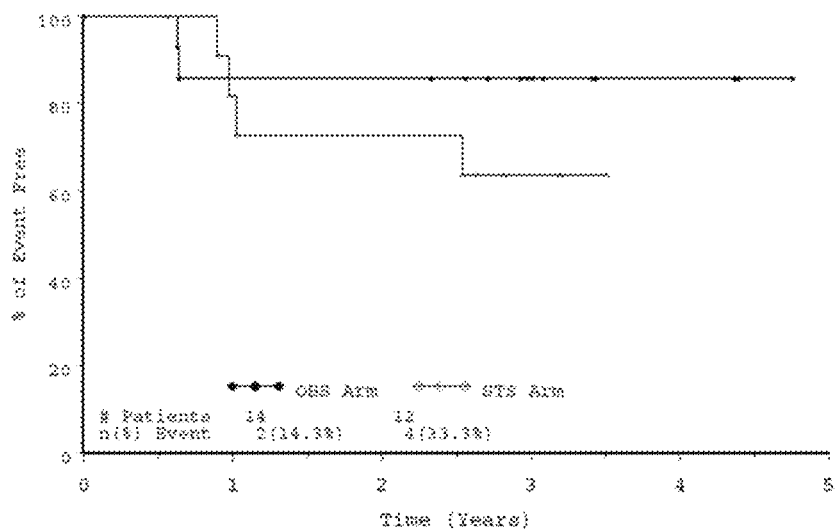
FIG. 24B is a Kaplan-Meier curve showing analysis of overall survival of patients having medulloblastoma tumors for the study of Example 1.
Figure 26A:
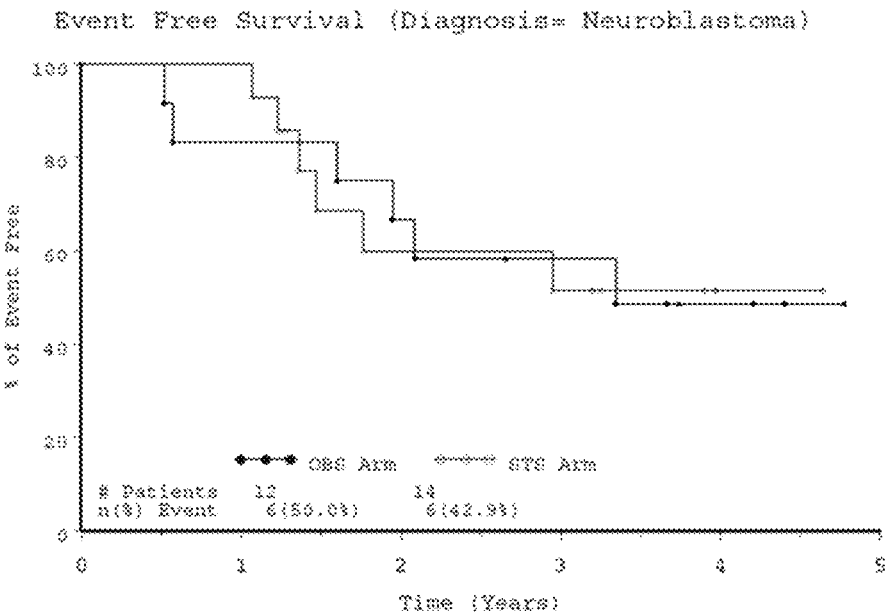
FIG. 26A is a Kaplan-Meier curve showing analysis of event free survival of patients having neuroblastoma tumors for the study of Example 1.
Figure 26B:
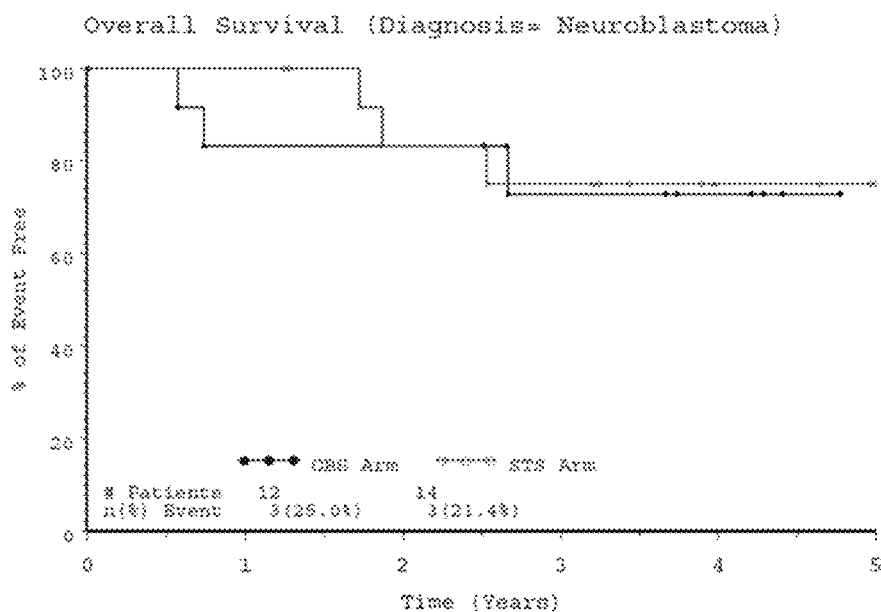
FIG. 26B is a Kaplan-Meier curve showing analysis of overall survival of patients having neuroblastoma tumors for the study of Example 1.
Figure 28A:
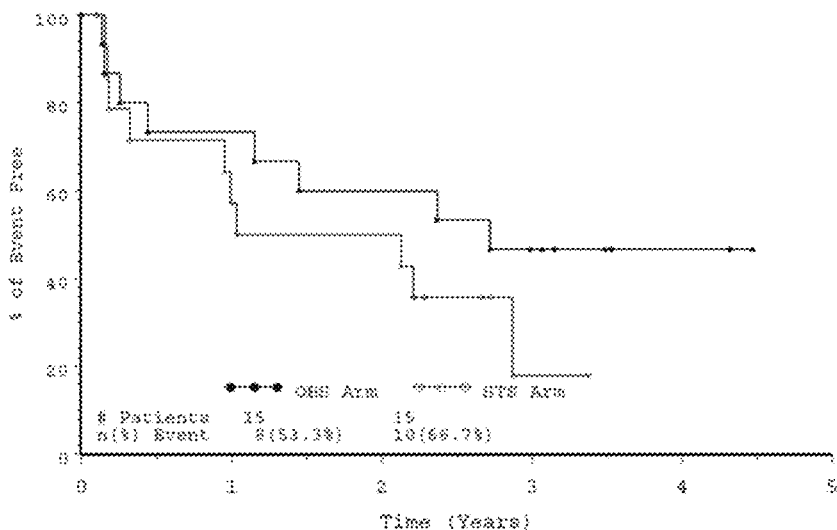
FIG. 28A is a Kaplan-Meier curve showing analysis of event free survival of patients having osteosarcoma tumors for the study of Example 1.
Figure 28B:
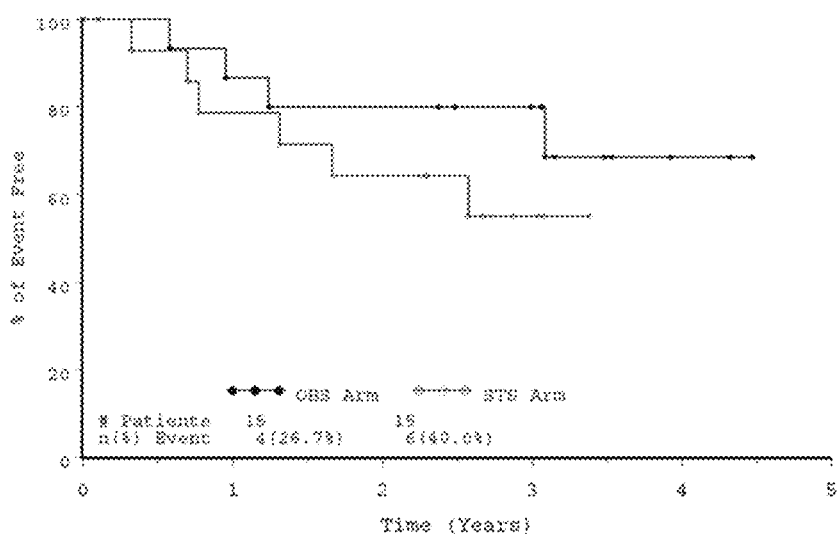
FIG. 28B is a Kaplan-Meier curve showing analysis of overall survival of patients having osteosarcoma tumors for the study of Example 1.
Figure 29A:
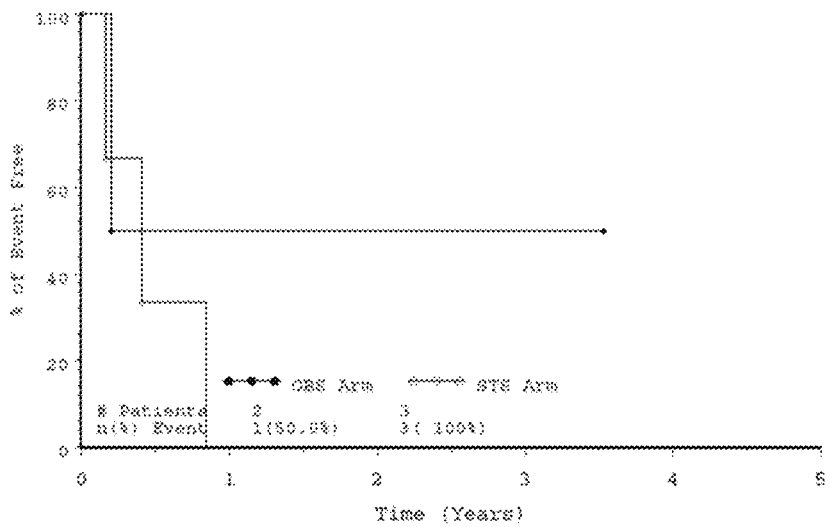
FIG. 29A is a Kaplan-Meier curve showing post-hoc analysis of event free survival excluding the group of other tumors for all patients for the study of Example 1.
Figure 29B:
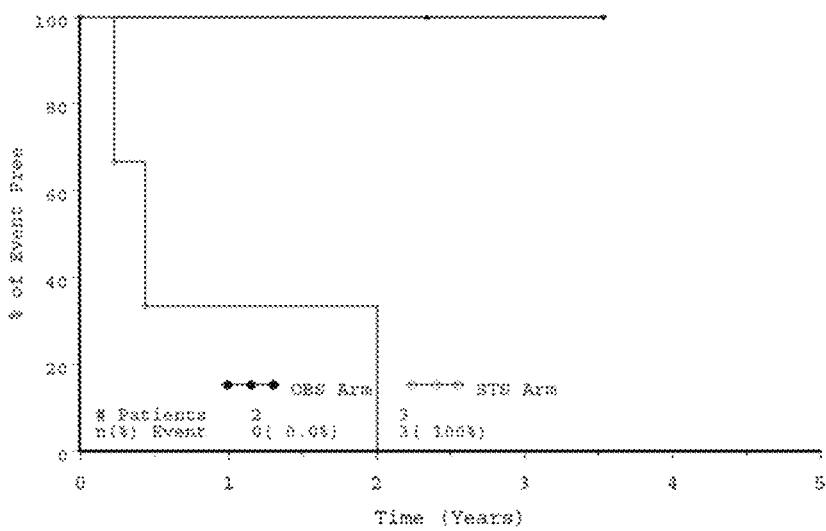
FIG. 29B is a Kaplan-Meier curve showing post-hoc analysis of overall survival excluding the group of other tumors for all patients for the study of Example 1.
Figure 32A:
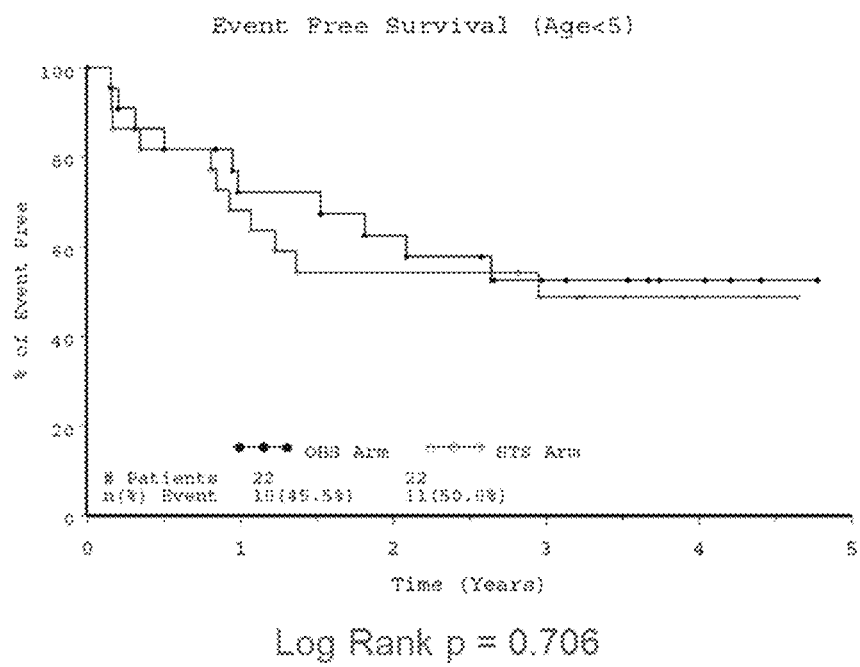
FIG. 32A is a Kaplan-Meier curve showing analysis of event free survival of patients under the age of 5 for the study of Example 1.
Figure 32B:
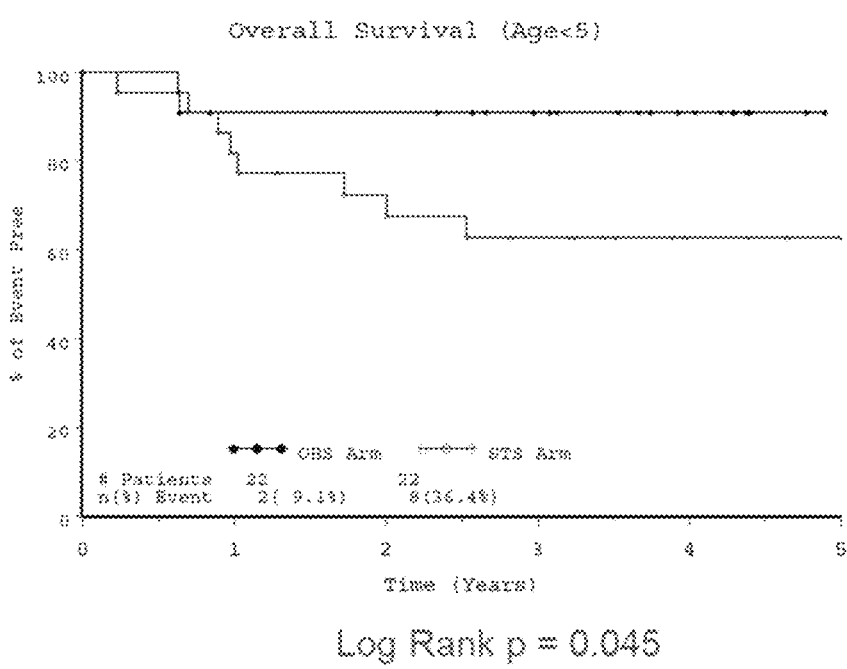
FIG. 32B is a Kaplan-Meier curve showing analysis of overall survival of patients under the age of 5 for the study of Example 1.
Figure 35A:
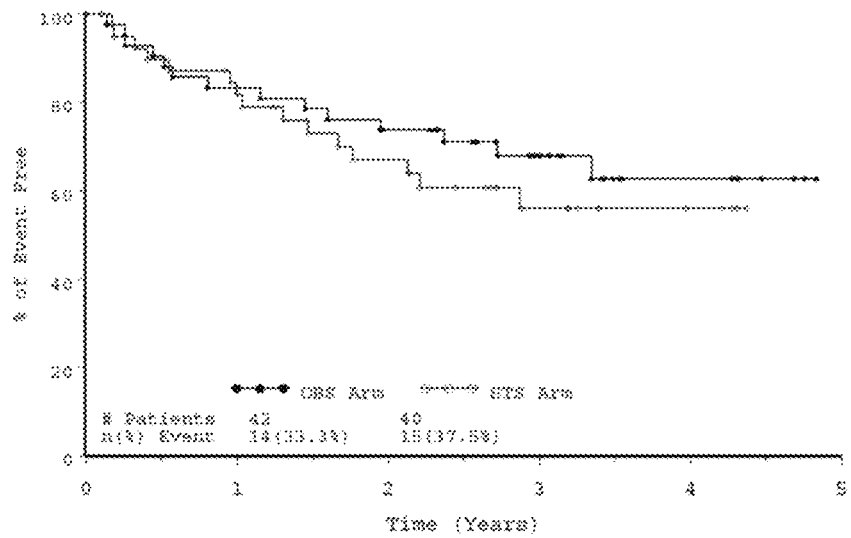
FIG. 35A is a Kaplan-Meier curve showing analysis of event free survival of patients greater than or equal to the age of 5 for the study of Example 1.
Figure 35B:
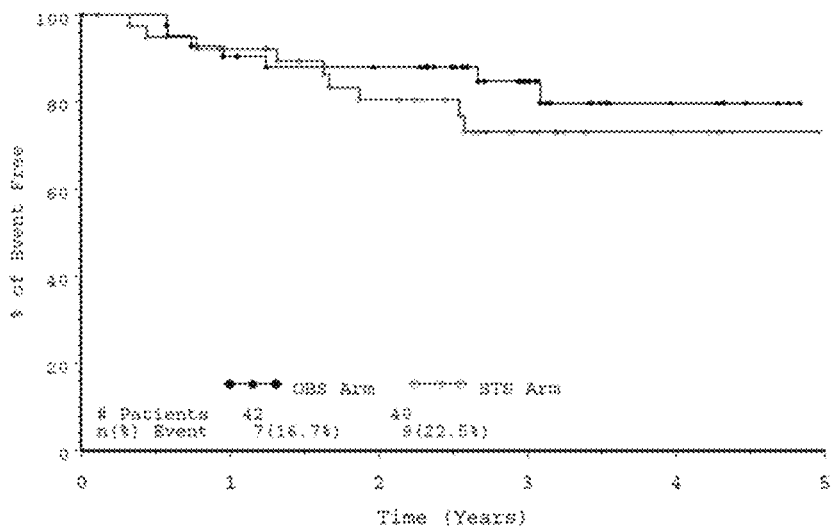
FIG. 35B is a Kaplan-Meier curve showing analysis of overall survival of patients greater than or equal to the age of 5 for the study of Example 1.

The term "patient" refers to any subject including mammals and humans. The patient may have a disease or suspected of having a disease and as such is being treated with a drug. In some instances, the patient is a mammal, such as a dog, chicken, cat, horse, or primate. In some instances, the term "patient," as used herein, refers to a human (e.g., a man, a woman, or a child). In some instances, the term "patient," as used herein, refers to laboratory animal of an animal model study. The patient or subject may be of any age, sex, or combination thereof In some embodiments as described further herein, the patient is treated with a platinum based chemotherapeutic such as cisplatin followed by administration of the drug sodium thiosulfate.

The term "pediatric patient" refers to a pediatric mammal and human. In some instances, the patient is a mammal, such as a dog, chicken, cat, horse, or primate or a puppy, a chic, a kitten, a colt or filly, or an infant. The pediatric patient may be of any ethnicity or sex. The pediatric patient may be of any age, which would be understood to the person of skill in the art to be a pediatric patient in medicine and in veterinary medicine. For example, a human pediatric patient may be a neonate up to 21 years of age. A newborn pediatric is understood to be birth to 1 month of age; an infant is 1 month to 2 years of age; a child is 2 years to 12 years of age; and an adolescent is 12 to 21 years of age. The pediatric patient may have a disease or suspected of having a disease and as such is being treated with a drug. In some embodiments as described further herein, the pediatric patient is treated with a platinum based chemotherapeutic such as cisplatin followed by administration of the drug sodium thiosulfate.

The term "ototoxicity" refers to any type of toxicity that affects the ear. The toxicity may be to the cochlea (e.g., cochleotoxicity), cochlear hair cells, the auditory nerve, or the vestibular system or any of these systems found in the ear or any of these systems in combination. The toxicity can manifest as hearing loss, sensorineural hearing loss, dysequilibrium, tinnitus, or hearing sensitivity or combinations thereof. When referring to hearing loss, the amount of toxicity causing the hearing loss can be mild, moderate, severe, profound, or total resulting in complete deafness. Alternatively, the hearing loss may present at specific frequencies including both high and low frequencies and all iterations of frequencies normal to mammalian hearing. The toxicity can be unilateral, bilateral, bilateral symmetric, or bilateral asymmetric with one ear being more affected than the other.

The terms "biological sample" or "sample" as used herein refers to a sample obtained or derived from a patient. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), urine, fluids of the eye (e.g., vitreous fluid, aqueous humor), lymph fluid, lymph node tissue, spleen tissue, bone marrow, and fluid from the auditory cavity.

As described herein, it was found that STS reduces ototoxicity in pediatric patients being treated with a platinum based chemotherapeutic. It was further surprisingly found that children being under the age of 12 have higher rates of ototoxicity and children under the age of 5 are even more at risk. It was further found that the administration of STS after a platinum based chemotherapeutic (i.e., cisplatin) was able to significantly reduce ototoxicity in these pediatric patients. In particular, it was discovered that STS could reduce the severity of ototoxicity, such as Brock grade 2 and 3 ototoxicities. Further, it was identified that the total amount of cisplatin exposure or cumulative dose did not interfere with STS mediated otoprotection. In addition, it was discovered that STS is highly suitable as an otoprotective drug when used in conjunction with local (non-disseminated) cancers.

STS is a water-soluble thiol compound with reducing agent properties and is commercially available as an established antidote for acute cyanide poisoning. STS is a reducing agent and has been used in oncology for preventing cisplatin nephrotoxicity, carboplatin ototoxicity and as an antidote for extravasation of various chemotherapy agents. The mechanism by which sodium thiosulfate reduces the nephrotoxicity caused by cisplatin and the ototoxicity by carboplatin is not fully understood. Proposed mechanisms of action involve its thiol group, which allow it to act as a free radical scavenger and/or by covalent binding inactivating the platinum compound. Sodium thiosulfate reacts irreversibly with cisplatin to form $Pt(S_2O_3)_4$ when the drugs are given simultaneously or in close approximation. It is also believed that sodium thiosulfate protects against nephrotoxicity by reducing delivery of cisplatin to the kidneys and by neutralizing cisplatin in the kidneys where sodium thiosulfate is highly concentrated. Following IV injection, sodium thiosulfate is distributed throughout the extracellular fluid. Some sodium thiosulfate is converted to sulfate in the liver. Up to 95% is excreted unchanged in the urine. The biological half-life is 0.65 hours (range: dependent on dose 16.5-182 minutes). When given intravenously, STS is rapidly excreted by the kidney.

Whilst not being bound by any theory, it is believed that the biological effects of STS in preventing cisplatin-induced ototoxicity include STS binding of electrophilic platinum molecules, scavenging of reactive oxygen species and its concentration in cochlear endolymph. Thus, a single effective dosage scavenges all remaining platinum chemotherapeutic so that it cannot accumulate and cause damage to the cochlear hair. Despite its cisplatin binding properties, the results from two phase III clinical trials further demonstrated that the efficacy of cisplatin based chemotherapeutics in pediatric patients was not affected when the STS was administered after administration of cisplatin.

In addition, STS does not adversely affect the efficacy of several other non-platinum based chemotherapeutics including doxorubicin and etoposide. In vitro studies of small cell lung cancer cell cultures showed no reduction of cytotoxicity for etoposide with either the immediate or delayed addition of STS followed by incubation for 72 hours. Similar studies showed no reduction of anti-tumor activity by STS for doxorubicin, carmustine (BCNU), paclitaxel or methotrexate. Owing to its ability to scavenge free platinum containing compounds, STS was extensively tested in the clinic, as further described in the Examples herein, and found to be a highly effective otoprotective compound for pediatric patients.

Described herein are methods for reducing ototoxicity in patient (i.e., pediatric patients) having a cancer and who are receiving a platinum based chemotherapeutic for treatment of the cancer. The methods include administering an effective amount of STS to the patient. It was found that STS significantly reduces the risk of ototoxicity particularly in pediatric patient populations. Therefore, one embodiment, described herein is a method for reducing ototoxicity in a pediatric patient having a cancer and receiving a platinum based chemotherapeutic comprising administering an effective amount of STS to the pediatric patient. In some aspects, the pediatric patient already has incurred ototoxicity and the administration of STS reduces the amount of future ototoxicity incurred by the pediatric patient.

The risk of a pediatric patient having detectable ototoxicity, for example, hearing loss measured by the Brock scale of ≥1 is significantly reduced by treatment with STS following the administration of a cisplatinum based chemotherapeutic. The risk of ototoxicity is relevant to a pediatric patient not receiving STS. Thus, in some embodiments, the likelihood of a pediatric patient incurring any ototoxicity is reduced by STS administration by about 10% to about 100%, about 30% to about 90% or about 40% to about 70%, including each integer within the specified ranges. In some embodiments, the risk of a pediatric patient incurring any ototoxicity is reduced by STS administration by about 10%, about 20%, about 30%, about 40%, about 50%, about 60%, about 70%, about 80%, about 90%, or even about 100%. In some aspects, the risk of a pediatric patient incurring ototoxicity according to ASHA-defined hearing loss criteria is about 50%.

Similarly, treatment of a pediatric patient with STS can further reduce long-term ototoxicity in pediatric patients having a cancer and receiving a platinum based chemotherapeutic. It is known that following treatment with STS, pediatric patients can exhibit ototoxicity weeks, months, or even years following the succession of treatment with the platinum based chemotherapeutic. Thus, another embodiment described herein is a method of reducing long-term ototoxicity in a pediatric patient having a cancer and receiving a platinum based chemotherapeutic comprising administering an effective amount of sodium thiosulfate to the pediatric patient.

As described above, it is thought that platinum based chemotherapeutic agents, such as cisplatin, exert ototoxic effects by concentrating in the aural cavity of a patient (e.g., a pediatric patient). It is further contemplated herein that STS can reduce the amount of platinum based chemotherapeutic agent in the aural cavity by binding to the agent and reducing its accumulation in the aural cavity. Another embodiment described herein is a method of reducing a concentration of cisplatin in an aural cavity of a pediatric patient having a cancer and receiving a platinum based chemotherapeutic comprising administering an effective amount of sodium thiosulfate to the pediatric patient. In some aspects, the concentration of cisplatin is reduced by in the aural cavity by about 50%, about 60%, about 70%, about 80%, about 90%, or about 100% compared to a pediatric patient receiving a platinum based chemotherapeutic and not receiving STS. In some aspects, the concentration of cisplatin is not detectable in the aural cavity. In some aspects, the patient administered STS is less susceptible to incurring ototoxicity because the amount of platinum based chemotherapeutic in the aural cavity is reduced. Methods for detecting cisplatin in the aural cavity include extracting a sample from the aural cavity and measuring the amount of cisplatin present in the sample, for example, through high performance liquid chromatography (HPLC) or other methods known in the art.

The methods described herein are also useful for preventing or inhibiting ototoxicity in a pediatric patient having a cancer and who is receiving a platinum based chemotherapeutic for treatment of the cancer. It was found that pediatric patients are particularly susceptible to incurring ototoxicity and prophylactically treating the pediatric patient can reduce the ototoxicity in the pediatric patient. Therefore, another embodiment described herein is a method of prophylactically treating a pediatric patient having a cancer and receiving a platinum based chemotherapeutic with an effective amount of STS, wherein the treatment reduces a likelihood of the pediatric patient incurring ototoxicity.

It has been determined that certain genetic variations can cause an increased likelihood of a pediatric patient having ototoxicity and the severity of ototoxicity in the patient. The genes TPMT, COMT, and ABCC3 have been shown to put pediatric patients at a greater risk for incurring ototoxicity (see Ross, C.J. et al. Genetic variants in TPMT and COMT are associated with hearing loss in children receiving cisplatin chemotherapy. *Nat. Genet.* 41, 1345-1349 (2009) and Pussegoda, K. et al. Replication of TPMT and ABCC3 genetic variants is highly associated with cisplatin-induced hearing loss in children. *Clin. Pharmacol. Ther.* 94, 243-251

(2013)). In addition, it has more recently been shown that single nucleotide polymorphism in the ACYP2 gene at the locus rs1872328 are associated with cisplatin-based ototoxicity (see Xu, K. et al. Common variants in ACYP2 influence susceptibility to cisplatin-induced hearing loss. *Nat. Genetics.* 47(3), 263-266 (2015). Thus, in some embodiments a pediatric patient receiving a cisplatin based chemotherapeutic is identified as being at high risk for having a genetic variation in one or more of the genes TPMT, COMT, ABCC3, and ACYP2 and treated with STS to reduce the likelihood, prevent, inhibit, or treat ototoxicity.

In some embodiments described herein, the pediatric patient has a cancer and is receiving a platinum based chemotherapeutic. In some other embodiments, the pediatric patient does not yet have a diagnosed cancer but is being treated with a platinum based chemotherapeutic. Any platinum-based drug would be expected to be scavenged by STS and reduce ototoxicity. Thus, in some embodiments, the platinum based chemotherapeutic comprises cisplatin, carboplatin, oxaliplatin, nedaplatin, triplatin tetranitrate, phenanthriplatin, picoplatin, and satraplatin. In some aspects, the platinum based chemotherapeutic is cisplatin.

The amount of platinum based chemotherapeutic that a pediatric patient is recieving is determined by the treating physician, the type of disease or cancer that is being treated, and the age or weight of the pediatric patient. In some aspects, the amount of platinum based chemotherapeutic (e.g., cisplatin) per cycle of administration is about 1 mg/kg to about 5 mg/kg, including each integer within the specified range. In some aspects, the amount of platinum based chemotherapeutic (e.g., cisplatin) per cycle of administration is about 10 mg/m$^2$ to about 300 mg/m$^2$, 10 mg/m$^2$ to about 100 mg/m$^2$, or about 40 mg/m$^2$ to about 80 mg/m$^2$, including each integer within the specified ranges.

Many cancers are treated with platinum based chemotherapeutics in pediatric patients, for which STS may be administered. In some aspects of the embodiments described herein, a pediatric patient has a cancer that is being treated with a platinum based chemotherapeutic followed by STS, wherein the cancer is localized or disseminated. In some aspects, the cancer is low-risk, medium risk, or high risk (e.g., metastatic) cancer. In some aspects, the cancer is low-risk or medium-risk. In some aspects, the cancer being treated with a platinum based chemotherapeutic is localized and is not disseminated or metastatic. Non-limiting and exemplary cancers that can be treated with a platinum based chemotherapeutic followed by STS comprise germ cell tumors (e.g., testicular cancer or ovarian cancer), hepatoblastoma, medulloblastoma, neuroblastoma, and osteosarcoma. In some aspects, a pediatric patient has a hepatoblastoma cancer and is being treated with a platinum based chemotherapeutic and STS. In some aspects, a pediatric patient has a low-risk or medium-risk hepatoblastoma cancer and is being treated with a platinum based chemotherapeutic and STS.

In some embodiments, the STS is administered to a pediatric patient receiving treatment with a platinum based chemotherapeutic agent prior to, concurrently with, or after the administration of the platinum based chemotherapeutic. In some aspects, the STS is administered 0 minutes or about 5 minutes to about 96 hours after the administration of the platinum based chemotherapeutic, including each integer of time within the specified range. In some aspects, the STS is administered about 30 minutes to about 24 hours, about 1 hour to about 24 hours, about 1 to about 12 hours, about 1 hour to about 8 hours, or about 4 hours to about 7 hours after the administration of the platinum based chemotherapeutic, including each integer of time within the specified ranges. In one aspect, the STS is administered about 6 hours after the administration of the platinum based chemotherapeutic.

The administration of STS may be carried out in any way that is known for administering STS. For example, STS may be administered parenterally or enterally. If administered parenterally, the STS can be administered intravenously (IV), subcutaneously (SC), or intramuscularly (IM). Enteral administration includes oral, sublingual or rectal. In embodiments, the STS is administered intravenously.

An effective amount of STS is an amount of STS, which prevents, reduces, or inhibits ototoxicity in a pediatric patient receiving a platinum based chemotherapeutic. In some embodiments, the amount of STS administered is about 0.5 g/m$^2$ to about 50 g/m$^2$, about 1 g/m$^2$ to about 25 g/m$^2$ or 15 g/m$^2$ to about 25 g/m$^2$, including each integer within the specified ranges. In some embodiments, the amount of STS administered is about 1 g/m$^2$, about 2 g/m$^2$, about 4 g/m$^2$, about 6 g/m$^2$, about 8 g/m$^2$, about 10 g/m$^2$, about 15 g/m$^2$, about 20 g/m$^2$, about 25 g/m$^2$, about 30 g/m$^2$, about 40 g/m$^2$, or about 50 g/m$^2$. The effective amount of STS is administered prior to, concomitantly with, or following each cycle of platinum based chemotherapy.

Some additional embodiments described herein are dosing regimens for treating a cancer in a pediatric patient, which include administering a platinum based chemotherapeutic and STS. One embodiment is a dosing regimen for treating hepatoblastoma in a pediatric patient that includes administering a dose of about 1 mg/kg to about 5 mg/kg or about 10 mg/m$^2$ to about 300 mg/m$^2$ per cycle of a platinum based chemotherapeutic, including each integer within the recited range; and also administering about 5 g/m$^2$ to about 25 g/m$^2$ of STS per cycle of the platinum based chemotherapeutic, including each integer within the specified ranges. In one aspect, the STS is administered from about 2 hours to about 6 hours after the administration of the platinum based chemotherapeutic, including each integer within the recited range.

The measurement of ototoxicity following administration of the platinum based chemotherapeutic and STS should be carried out after a period time following the last treatment with the platinum based chemotherapeutic and STS. In some aspects, the ototoxicity is measured after a time period of at least 3 days to about 3 months, 1 week to about 3 months, 1 week to about 2 months, or 1 week to about 4 weeks following the last treatment with the platinum based chemotherapeutic and STS, including each integer within the specified ranges of time. In one aspect, the ototoxicity is measured after a time period of at least 4 weeks from the last treatment with the platinum based chemotherapeutic and STS.

The measurement of ototoxicity following administration of the platinum based chemotherapeutic and STS can be carried out multiple times and up to years following the last administration of STS and the platinum based chemotherapeutic. Audiometric methods for measuring hearing loss are well known to those of ordinary skill in the art and are used in conjunction with various scales to assess ototoxicity. Assessing ototoxicity allows, for example, the assessment of any potential ototoxicity or long-term prevention of ototoxicity by STS. The assessment of ototoxicity can be determined by one or more criteria known in the art. For example, ototoxicity may include assessment by the tinnitus functional index, Brock grading, Children's Cancer Group 1996 study scale, Children's Hospital Boston scale, the Chang and Chinosornvatana scale, the American Speech-Language-Hearing Association criteria, the Common Terminology Criteria for Adverse Events scale (CTCAE pediatric grading), or the International Society of Pediatric Oncology Boston Ototoxicity Scale or a combination of these scales (see Gurney, J.G. et al., Oncology, J. Clin. Onc. 30(19), 2303-2306 (2012). The measurement of hearing function should in most cases be completed prior to treatment with an ototoxic drug such as a cisplatin or another platinum based chemotherapeutic. This establishes a baseline measure of hearing function to which any potential ototoxic effects can be compared. Thus, changes in hearing or increase or decrease in ototoxicity is computed relative to baseline measures prior to the patient receiving a platinum based chemotherapeutic or sodium thiosulfate or both.

The Brock scale is defined as follows: a <40 dB hearing loss at all frequencies, which indicates a grade 0 or minimal hearing loss; a ≥40 dB hearing loss at 8,000 Hz only, which indicates a grade 1 or mild hearing loss; a ≥40 dB hearing loss at 4,000 Hz and above, which indicates a grade 2 or moderate hearing loss; a ≥40 dB hearing loss at 2,000 Hz and above, which indicates a grade 3 or marked hearing loss; or a ≥40 dB hearing loss at 1,000 Hz and above, which indicates a grade 4 or severe hearing loss.

The CTCAE scale is Based on hearing at 1,2,3,4,6, & 8 kHz. Grade 1 is a threshold shift >20 dB at 8kHZ in at least 1 ear; Grade 2 is a threshold shift >20 dB at 4kHz and above in at least 1 ear; Grade 3 is hearing loss sufficient to indicate therapeutic intervention including hearing aids, a threshold shift >20 dB at 3kHz and above in at least 1 ear; speech and language svcs indicated; and grade 4 is the audiologic indication of cochlear implant and speech and language svcs indicated.

The Children's Cancer Group 1996 scale is defined as follows: ≥40 dB HL loss at 6,000 and/or 8,000 Hz is indicative of grade 1, >25 dB HL loss at 3,000 and/or 4,000 Hz is indicative of grade 2, >25 dB HL loss at 2,000 Hz is indicative of grade 3; and a ≥40 dB HL loss at 2,000 Hz is indicative of grade 4. Children's Hospital Boston scale is defined as follows: <20 dB hearing loss at frequencies 500-8,000 Hz; no functional hearing loss; >20 dB hearing loss above 4,000 Hz; functional loss: slight hearing loss that may result in decreased musical appreciation indicative of a grade 1; >20 dB hearing loss at 4,000 Hz and above; functional loss: educationally significant hearing loss indicative of grade 2; >20 dB hearing loss at 2,000 Hz and above; functional loss: severe hearing loss requiring hearing aids indicative of grade 3.

The Chang and Chinosornvatana scale is defined as ≤20 dB at 1, 2, and 4 kHz is indicative of normal hearing; (1a) ≥40 dB at any frequency 6 to 12 kHz; (1b) >20 and <40 dB at 4 kHz is indicative of grade 1a and 1b, respectively; (2a) ≥40 dB at 4 kHz and above; (2b) >20 and <40 dB at any frequency below 4 kHz is indicative of grade 2a and 2b, respectively; ≥40 dB at 2 or 3 kHz and above is indicative of grade 3; and ≥40 dB at 1 kHz and above is indicative of grade 4.

The American Speech-Language-Hearing Association criteria is defined as (1) ≥20 dB decrease at any one frequency; (2) ≥10 dB decrease at two or more adjacent frequencies; or (3) loss of response at three adjacent frequencies at which responses were previously obtained. The ASHA further specifies that a significant change in hearing sensitivity must be confirmed by repeat testing to be considered valid.

International Society of Pediatric Oncology Boston Ototoxicity Scale is defined as ≤20 dB HL at all frequencies is indicated to be normal hearing; >20 dB HL (ie, 25 dB HL or greater); SNHL above 4,000 Hz (ie, 6 or 8 kHz) is indicated to be grade 1; >20 dB HL SNHL at 4,000 Hz and above is indicated to be grade 2; >20 dB HL SNHL at 2,000 Hz or 3,000 Hz and above is indicated to be grade 3; and >40 dB HL (i.e., 45 dB HL or more) SNHL at 2,000 Hz is indicated to be grade 4.

The tinnitus functional index is a questionnaire-based index which quantitates the severity of tinnitus symptoms (see Henry JA et al., *Audiology Today* 26(6), pp. 40-48 (2014). The index is defined as follows: a mean score of 14 (range of 0-17) is no tinnitus, a mean score of 21 indicates a low levels of tinnitus; a mean score of 42 is a moderate tinnitus; a mean score of 65 is high levels of tinnitus, and a mean score of 78 is large levels of tinnitus. Ranges can be broken down into <25 is relatively mild tinnitus or no tinnitus, 25-50 indicates significant problems with tinnitus, and >50 indicates levels of tinnitus that require aggressive intervention.

In some embodiments, the ototoxicity is measured by measuring hearing loss at one or more frequencies comprising 500 Hz, 1,000 Hz, 2,000 Hz, 4,000 Hz, or 8,000 Hz or a combination of frequencies thereof, wherein a change in hearing is computed relative to baseline measures prior to the patient receiving a platinum based chemotherapeutic or sodium thiosulfate or both. In some aspects, an increase in ototoxicity can be determined as a reduction in hearing measured by a 20 dB loss at a single frequency; a reduction in hearing measured by a 10 dB loss at two consecutive frequencies; or a loss of response at three consecutive test frequencies where responses were previously obtained. In some further aspects, an increase in ototoxicity is measured as a reduction in bilateral high-frequency hearing characterized by: a <40 dB hearing loss at all frequencies, which indicates a grade 0 or minimal hearing loss; a ≥40 dB hearing loss at 8,000 Hz only, which indicates a grade 1 or mild hearing loss; a ≥40 dB hearing loss at 4,000 Hz and above, which indicates a grade 2 or moderate hearing loss; a ≥40 dB hearing loss at 2,000 Hz and above, which indicates a grade 3 or marked hearing loss; or a ≥40 dB hearing loss at 1,000 Hz and above, which indicates a grade 4 or severe hearing loss. In still some further aspects, an increase in ototoxicity is measured as a reduction in hearing characterized by: a ≤20 dB hearing loss at all frequencies, which indicates a grade 0 hearing loss; a >20 dB HL above 4,000 Hz, which indicates a grade 1 hearing loss; a >20 dB HL at 4,000 Hz and above, which indicates a grade 2 hearing loss; a >20 dB HL at 2,000 Hz or 3,000 Hz, which indicates a grade 3 hearing loss; or a >40 dB HL at 2,000 Hz and above, which indicates a grade 4 hearing loss. In some other aspects, an increase in ototoxicity can be measured by a reduction in a tinnitus functional index.

The administration of STS to pediatric patients being treated with a platinum based chemotherapeutic was found to not exacerbate renal or other toxicities. Thus, in some aspects, patients receiving STS do not experience more severe or an increased incidence rate of adverse events compared to patients not administered STS. These adverse events comprise grade 3 or grade 4 neutropenia, reduced glomerular filtration rates, increased serum creatinine, infection, hypomagnesemia, hypernatremia, vomiting, or nausea. In some other aspects, pediatric patients administered STS do not have a reduction in relapse free survival or overall survival compared to patients not administered STS.

The methods described herein are well suited for reducing or preventing ototoxicity or reducing the likelihood of incurring ototoxicity in any pediatric patient of any age. Therefore, in some embodiments described the pediatric patient being treated following the methods described herein may be a new born or the pediatric patient may about 1 month old, about 2 months old, about 3 months old, about 4 months old, about 5 months old, about 6 months old, about 7 months old, about 8 months old, about 9 months old, about 10 months old, about 11 months old, about 12 months old, about 1 year old, about 1.5 years old, about 2 years old, about 2.5 years old, about 3 years old, about 3.5 years old, about 4 years old, about 4.5 years old, about 5 years old, about 5.5 years old, about 6 years old, about 6.5 years old, about 7 years old, about 7.5 years old, about 8 years old, about 8.5 years old, about 9 years old, about 9.5 years old, about 10 years old, about 10.5 years old, about 11 years old, about 11.5 years old, about 12 years old, about 12.5 years old, about 13 years old, about 13.5 years old, about 14 years old, about 14.5 years old, about 15 years old, about 15.5 years old, about 16 years old, about 16.5 years old, about 17 years old, about 17.5 years old, about 18 years old, about 18.5 years old, about 19 years old, about 19.5 years old, about 20 years old, about 20.5 years old, or about 21 years old. In some aspects, the pediatric patient is about 12 years of age or less, about 5 years of age or less, about 2 years of age or less, or about 1 year of age or less.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1 Study of Sodium Thiosulfate to Reduce Ototoxicity in Pediatric Patients Recieving Cisplatin The study was designed as a multicentre, randomised, open-label, phase 3 clinical trial. Patients were enrolled at 38 participating Children's Oncology Group (COG) hospitals in the USA and Canada. Written consent or assent from participants or their legal guardians were obtained before registration. The study was approved by the US National Cancer Institute (NCI) Central Institutional Review Board and site institutional review boards. Co-enrollment onto a companion observational cohort study of ototoxicity grading scales was mandatory. Participants in the study were aged 1-18 years at study entry and were newly diagnosed with hepatoblastoma, germ cell tumour, medulloblastoma or CNS primitive neuroectodermal tumour, neuroblastoma, osteosarcoma, or other cancer types treated with cisplatin.

Key eligibility criteria included planned cumulative cisplatin dose of 200 $mg/m^2$ or more and infusion duration of 6 h or less; performance score of 50 or more by the Karnofsky (>16 years) or Lansky (≤16 years) scales; no previous cisplatin or carboplatin treatment; no known thiol hypersensitivity; and normal institutional laboratory values reflecting haematological, renal, and hepatic function. Normal hearing was required before enrolment as defined by hearing thresholds of 20 dB hearing level (HL) or less at 500-8000 Hz when measured with earphones or 25 dB HL or less when measured in the sound field, or as defined by brainstem auditory evoked response thresholds equivalent to behavioural thresholds of 20 dB HL or less. Previous cranial irradiation was initially not allowed but later permitted, provided hearing was normal, by a protocol amendment (Mar. 31, 2010) to augment trial recruitment. Patients were not eligible if they were registered on a cancer directed COG therapeutic study to avoid potential confounding of the primary aims by the ACCL0431 randomization.

Patient Randomization

Patients were enrolled and randomly assigned to either the sodium thiosulfate or observation (control group) up to 5 days before they received any cisplatin. The allocation sequence for each stratum according to a permuted block algorithm was generated, where each block of four contained two sodium thiosulfate and two control randomizations. The randomization was centrally computer-generated by the COG trial management system. Allocation was electronically concealed to all investigators, clinicians, and participants. Site research staff did the enrolment, entering eligibility confirmation and specification of stratification factors into the COG trial management system, and receiving the electronically generated allocation for the site. Randomization was 1:1 and was initially stratified into four groups defined by age (<5 years or ≥5 years) and duration of cisplatin infusion (<2 h or ≥2 h). Later, we added one separate stratum for eligible participants who had previously received cranial irradiation, irrespective of age or duration of cisplatin infusion. Randomization was masked for central reviewers of audiometry data, but was not placebo controlled for participants or treating clinicians to minimise complexity and cost for participating sites.

Procedures

Cisplatin was administered as specified by each participant's cancer treatment plan. For participants randomly assigned to the control group, the cisplatin containing treatment regimen alone was to be administered. Participants in the sodium thiosulfate group received sodium thiosulfate daily over 15 min beginning 6 h after the completion of each cisplatin dose. The protocol specified sodium thiosulfate dose was 16 $g/m^2$ (533 mg/kg where the cisplatin dose was calculated by bodyweight) administered as a 12.5% solution. This sodium thiosulfate dose was selected because it was within the published effective dose range and was well tolerated by children. For participants receiving multiday cisplatin regimens, a documented serum sodium concentration of less than 145 mEq/L was required before each sodium thiosulfate dose, and a minimum of 10 h was to have elapsed between sodium thiosulfate and the next cisplatin dose. Otherwise, no modifications of dose or administration of sodium thiosulfate or other chemotherapy drugs were made. Protocol guidelines for supportive care during the sodium thiosulfate infusion included routine administration of antiemetics, limited blood pressure monitoring, and, if applicable, administration of low-dose meperidine to manage infusion-related rigors. Concurrent use of other ototoxic drugs (eg, aminoglycosides and loop diuretics) was discouraged by protocol for all participants but captured in data reporting.

Cisplatin dose modifications were not captured as participants did not receive cancer treatment according to specified protocols. Hearing assessments were done at baseline, up to 8 days before each cisplatin course, 4 weeks after completion of the final cisplatin course, and 1 year later. Audiometry included measurement of bilateral pure tone air conduction thresholds at 500-8000 Hz with earphones or in the sound field using paediatric hearing assessment methods; otoscopy; immittance evaluation of middle ear function; and evoked otoacoustic emissions, if available. For participants unable to cooperate due to very young age, developmental disability, or medical status, brainstem auditory evoked response thresholds were to be measured instead.

Audiological testing was completed using standard clinical audiometers, middle ear analyzers, evoked potentials systems, and evoked otoacoustic emission OAE systems (if available). All equipment was calibrated in accordance with guidelines set forth by the American Speech-Language-Hearing Association. Audiological evaluations was performed at baseline (prior to the first dose of cisplatin), prior to each cisplatin course, and both 4 weeks and 1 year after completion of the final course of cisplatin. Patients who proceeded to hematopoietic stem cell transplant following an Induction Phase that includes cisplatin had audiological evaluations as above during the Induction Phase, 4 weeks after completion of the final cisplatin course during Induction (i.e., pre-transplant) and both 4 weeks and 1 year post transplant.

Audiological evaluations was conducted within 8 days and preferably within 72 hours, prior to each cisplatin infusion. Audiological testing included: (a) measurement of bilateral pure tone air conduction thresholds at 0.5-8 kHz; (b) otoscopy by audiologist or other healthcare professional; (c) immittance evaluation; and (d) measurement of evoked OAEs, if available. For patients too young to cooperate with standard audiometric measurements, BAER should be obtained instead. Additionally, UHF audiometry will be performed for patients 5 years of age or older at institutions where that modality is available. Measurement of UHF will be of bilateral pure tone air conduction thresholds at 9-16 kHz. In addition to institutional electronic entry of all required audiometry data, a copy of each audiogram was faxed for independent review by two expert paediatric audiologists for whom randomization was masked (KK, BB); differences in interpretation were resolved by consensus. Hearing loss was determined according to American Speech-Language-Hearing Association (ASHA) post hoc with a protocol-specific binary classification of localised versus disseminated.

Saliva or blood specimen were obtained from each participant who chose to assess mutations in the TPMT and COMT genes. Criteria for ending protocol treatment included completion of the cancer treatment regimen, premature discontinuation of cisplatin, administration of cranial irradiation after enrolment but before measurement of the primary endpoint, and inability to continue sodium thiosulfate. Participants off protocol treatment were followed up for all endpoints. Criteria for removal from the study included death, loss to follow-up, or entry onto another COG therapeutic study for the underlying cancer (in which case we obtained survival data from that therapeutic study).

Outcomes

The primary endpoint was hearing loss at 4 weeks after final cisplatin treatment, but before any haemopoietic cell transplantation, according to validated ototoxicity criteria. Participants were deemed not assessable for this outcome if it was found during central review that audiometry data derived from headphone, sound field, or brainstem auditory evoked response testing at baseline or post-treatment were missing, incomplete, or technically unsatisfactory.

Secondary endpoints were frequency-specific hearing loss at 4 weeks (for 500 Hz, 1000 Hz, 2000 Hz, 4000 Hz, and 8000 Hz), haematological and renal toxicity, event free survival (defined as the time from study enrolment until disease relapse or progression, diagnosis of a second malignant neoplasm, or death, whichever came first), and overall survival (defined as the time from enrolment to death or last date confirmed alive). By protocol amendment on Mar. 31, 2010, we added an exploratory secondary aim to assess the association of mutations in the TPMT and COMT genes with cisplatin-induced hearing loss and sodium thiosulfate effect.

Statistical analysis

The primary endpoint of hearing loss according to ASHA criteria compared the audiometric evaluation at enrolment (ie, baseline) with the first assessment done at least 4 weeks after the final dose of cisplatin (ie, post-treatment). Using a modified intention-to-treat approach, we analysed patients on the basis of their randomization assignment, irrespective of treatment received, but included only eligible participants who completed both baseline and post-treatment hearing assessments. The accrual goal was 108 participants with complete hearing evaluation allocated equally to the two study groups. We compared the proportion that developed hearing loss by treatment group using a one-sided $\chi^2$ test. We deemed a p value of 0.05 or less to be significant. Assuming a 4-week cumulative hearing loss incidence of 45% in the control group and an incidence of 22.5% in the sodium thiosulfate group, the study as designed would provide 80% power. The probability of hearing loss among patients in the control group was based on a contemporary paediatric report involving multiple tumour types. Reduction of this probability by half was deemed clinically relevant. Because participants who had received previous cranial irradiation were added through an amendment, we did a post-hoc sensitivity analysis that included only participants who were not enrolled in the new stratum. We also did a post-hoc analysis of hearing loss at the 1-year timepoint for participants who had interpretable audiometry data and had not had a survival event or haemopoietic cell transplantation; these participants were excluded due to the inability to control for additional ototoxic exposures.

We estimated the magnitude of the association between sodium thiosulfate assignment and hearing loss using the odds ratio (OR); p values for the test of OR=1 and corresponding 95% CI were derived using the Wald test for the parameter associated with the randomised treatment assignment from a logistic model. The logistic model was stratified according to the strata used for randomization. We estimated stratum-specific probabilities of hearing loss using the observed proportion of assessable participants in the particular stratum with hearing loss; we also calculated exact 95% CIs.

We planned interim monitoring for futility of an otoprotective effect of sodium thiosulfate. After we ascertained the primary outcome measure in the first 60 patients, we calculated the probability of rejecting the null hypothesis at the end of planned enrolment on the basis of observed hearing loss to that point and the assumption that development of hearing loss for future participants would follow the alternative hypothesis. If this conditional probability was 0.10 or less, the study was to be identified to the COG Data and Safety Monitoring Committee for closure due to lack of efficacy.

The change in hearing threshold between baseline and post-treatment timepoint at different frequencies (500 Hz, 1000 Hz, 2000 Hz, 4000 Hz, and 8000 Hz) was determined by the mean change, and assessed the hypothesis of no difference between groups using the Wilcoxon two-sample test for non-parametric data. We deemed a one-sided p value 0.05 or less to be significant; we made no adjustment for multiple comparisons for this assessment.

For haematological and renal toxicity, denominators represent the number of participants who completed the required toxicity assessment during each cycle. For both types of toxicity, we assessed the hypothesis of no difference in incidence using a $\chi^2$ test of proportions.

For event-free survival and overall survival, patients who did not have an event were censored at time of last contact. We estimated the probability of remaining event free as a function of time post-enrolment using the method of Kaplan and Meier. We compared risk of event across groups defined by randomised regimen using the log-rank statistic. We generated relative hazard ratios (RHR) and 95% CIs by fitting a relative-risk regression model, using partial likelihood where the model contained the characteristic of interest as the only variable. We computed survival estimates as 3-year event-free survival and 3-year overall survival. We did a post-hoc analysis of event-free survival and overall survival by extent of disease using the same methods. We considered all eligible participants in the survival analyses by intention to treat. We did all statistical calculations using SAS (version 9.4) or Stata (version 14).

Results

Between Jun. 23, 2008, and Sep. 28, 2012, 131 participants from 38 institutions were enrolled in the study, reaching the planned accrual goal (see scheme FIG. 1). Six participants were deemed ineligible; four because they were co-enrolled on a disease directed COG therapeutic study (with three participants randomly assigned to sodium thiosulfate and one to control), one because cranial irradiation was administered before reaching the primary endpoint (randomly assigned to control), and one because there was no source documentation of normal baseline serum electrolyte values (randomly assigned to sodium thiosulfate). Of the 125 eligible participants, 38 were enrolled before and 87 after the protocol amendment that allowed participants who had previously received cranial irradiation to enrol (n=9). 64 participants were randomly assigned to the control group and 61 to the sodium thiosulfate group. Interim monitoring resulted in recommendations to continue the trial as planned. Data current to Mar. 31, 2015, were used in this analysis.

Baseline characteristics were similar between treatment groups. The overall proportions of eligible participants with disseminated disease at study entry were similar; four eligible participants in each group had previously received cranial irradiation. The disease-specific characteristics of participants by randomization group with respect to age and extent of disease were balanced between groups. The median cumulative cisplatin dose for the control group was 387 mg/m$^2$ (IQR 305-466) and for the sodium thiosulfate group was 393 mg/m$^2$ (290-420). The median cumulative sodium thiosulfate dose was 95.8 g/m$^2$ (60.1-127.6). The proportions of participants who had received loop diuretics or aminoglycoside antibiotics were similar in the control (17 [27%] of 64 participants) and sodium thiosulfate (17 [28%] of 61 participants) groups. No participants underwent haemopoietic cell transplantation before assessment for the primary endpoint.

104 participants were assessable for post-treatment hearing loss at 4 weeks (55 of 64 participants in the control group and 49 of 61 in the sodium thiosulfate group). Of these assessable participants, 14 (29%) in the sodium thiosulfate group and 15 (27%) in the control group were younger than 5 years. Hearing loss was identified in 14 (28.6%; 95% CI 16.6-43.3) participants in the sodium thiosulfate group compared with 31 (56.4%; 42.3-69.7) in the control group (p=0.00022).

For participants younger than 5 years, the incidence of hearing loss was unexpectedly and substantially lower in the sodium thiosulfate group than in the control group (three [21.4%] of 14 participants [95% CI 4.7-50.8] vs 11 [73.3%] of 15 [44.9-92.2]); whereas the difference in incidence between groups was not as large for older patients (11 [31.4%; 16.9-49.3] of 35 vs 20 [50.0%; 33.8-66.2] of 40). The incidence of hearing loss was lower for participants in the sodium thiosulfate group than in the control group after cisplatin infusion of 2-6 h (ten [41.7%; 95% CI 22.1-63.4] of 24 vs 21 [70.0%; 50.6-85.2] of 30) and after cisplatin infusion of less than 2 h (four [16.0%; 4.5-36.1] of 25 vs ten [40.0%; 21.1-61.3] of 25). The stratum of previous cranial irradiation contained only eight assessable participants; hearing loss occurred in two (50%) of four sodium thiosulfate-treated participants versus four (100%) of four patients in the control group. When these eight irradiated participants were excluded in a post-hoc analysis, hearing loss was noted in 12 (26.7%; 95% CI 14.6-41.9) of 45 participants in the sodium thiosulfate group compared with 27 (52.9%; 38.5-67.1) of 51 in the control group (p=0.0045). By the logistic test adjusted for stratification variables, the likelihood of hearing loss was significantly lower in the sodium thiosulfate group compared with the control group (OR 0.31, 95% CI 0.13-0.73; p=0.0036). When the eight irradiated participants were removed from the analysis, the unadjusted OR was 0.32 (95% CI 0.13-0.76; p=0.010). Of the 104 participants assessable for hearing loss at the primary endpoint, 67 were also assessable at 1 year in a post-hoc analysis; of these, nine (28%) of 32 participants who received sodium thiosulfate had ASHA-defined hearing loss compared with 19 (54%) of 35 controls (p=0.0015). For the eight assessable participants who had previously received cranial irradiation, none of their hearing outcomes at 1 year were changed from the 4-week timepoint.

The mean change in hearing threshold within key frequencies is shown in the table below. For the sodium thiosulfate group, the change in hearing threshold from baseline to 4 weeks after cisplatin treatment was smaller than in the control group, although there was no significant difference between the groups.

| Mean change in hearing threshold within key frequencies | | | | | | |
|---|---|---|---|---|---|---|
| | Control | | STS | | | Change between |
| Hz | Mean (SD) | n | Mean (SD) | n | p-value | groups |
| 500 | −1.1 (8.6) | 45 | −1.5 (5.8) | 38 | 0.34 | 0.4 |
| 1000 | −0.3 (9) | 47 | −0.7 (4.6) | 37 | 0.36 | 0.4 |
| 2000 | 0.6 (12.7) | 47 | −1.2 (4.9) | 38 | 0.42 | 1.8 |

-continued

Mean change in hearing threshold within key frequencies

| | Control | | STS | | | Change between groups |
|---|---|---|---|---|---|---|
| Hz | Mean (SD) | n | Mean (SD) | n | p-value | |
| 4000 | 9.6 (20.5) | 47 | 1.1 (7.1) | 38 | 0.11 | 8.5 |
| 8000 | 17.0 (24.7) | 42 | 9.7 (17.3) | 37 | 0.18 | 7.3 |

*A negative value indicates a better mean hearing threshold compared with the baseline evaluation and a positive value indicates a poorer mean hearing threshold.

Haematological toxicity was not significantly different between the treatment groups, occurring in 137 (77%) of 177 participant cycles in the sodium thiosulfate group and 172 (77%) of 223 participant cycles in the control group (p=0.95). Aggregate nephrotoxicity was more common in the sodium thiosulfate group, in which 37 (25%) of 147 participant cycles were affected versus 25 (13%) of 187 controls (p=0.0059). Hypophosphataemia and hypokalaemia were more common in the sodium thiosulfate group than in the control group. Notably, no cases of either increased creatinine or reduced glomerular filtration rate met the CTCAE grade 3 threshold in either group.

The most common grade 3-4 haematological adverse events, irrespective of attribution, were neutropenia (117 [66%] of 177 participant cycles in the sodium thiosulfate group vs 145 [65%] of 223 in the control group), whereas the most common non-haematological adverse event was hypokalaemia (25 [17%] of 147 vs 22 [12%] of 187). As part of the NCI Adverse Event Reporting System, this study included expedited reporting of serious adverse events. Reporting was required only for participants randomly assigned to the sodium thiosulfate group. 194 serious adverse events were reported in 26 patients; of these, 112 were deemed unrelated, 62 unlikely, 20 possibly, and none probably or definitely related to sodium thiosulfate. 85 were non-haematological adverse events, of which 49 were deemed unrelated, 25 unlikely, 11 possibly, and none probably or definitely related to sodium thiosulfate; 70 were haematological adverse events, of which 53 were deemed unrelated, 13 were deemed unlikely, four possibly, and none probably or definitely related to sodium thiosulfate. Of the 194 serious adverse events, the three most common were decreased neutrophil count (26 [13%] in 14 participants), decreased platelet count (23 [12%] in 12 participants), and anaemia (21 [11%] in ten participants).

All 125 eligible patients were included in the analysis of event-free survival and overall survival. Median follow-up was 3.5 years (IQR 1.4-4.5) for event-free survival (median follow-up 3.4 years [IQR 2.9-4.3] for the sodium thiosulfate group, and 3.8 years [3.1-4.5] for the control group) and 3.5 years (1.5-4.5) for overall survival (median follow-up 3.4 years [2.9-4.3] for the sodium thiosulfate group, and 3.8 years [3.1-4.7] for the control group). Among the 61 participants assigned to sodium thiosulfate, 26 events and 17 deaths occurred; among the 64 participants in the control group, 24 events and ten deaths occurred. All events were relapse except for one participant in the sodium thiosulfate group who developed a second malignant neoplasm. As classified by site investigators, all deaths were deemed to be due to disease, except for one death in the sodium thiosulfate group that was attributed to cancer treatment-related sepsis but was not related to sodium thiosulfate. Considering the entire sample, no significant difference was noted between the sodium thiosulfate and control groups for event-free survival or overall survival (FIG. 2). 3-year event-free survival was 54% (95% CI 40-66) in the sodium thiosulfate group versus 64% (50-74) in the control group; 3-year overall survival was 70% (56-80) versus 87% (76-93).

Because of the possibility of an effect of sodium thiosulfate on survival that emerged for the sample as a whole, we did a post-hoc stratification of the sample by extent of disease at enrollment. Within the group deemed to have localised disease (n=77), we found no significant difference between treatment groups in event-free survival (median follow-up 3.4 years [IQR 3.2-4.3] for the sodium thiosulfate group, and 3.7 years [3.1-4.5] for the control group) or overall survival (median follow-up 3.5 years [3.2-4.3] for the sodium thiosulfate group, and 3.8 years [3.0-4.8] for the control group; FIG. 3). The 3-year event-free survival was 60% (95% CI 42-74) for the sodium thiosulfate group versus 66% (48-78) for the control group; 3-year overall survival was 83% (66-92) versus 89% (74-96). Among participants with localised disease, 14 events and six deaths in both the control and sodium thiosulfate groups occurred. Among participants deemed to have disseminated disease (n=47), we found no difference between treatment groups in event-free survival (median follow-up 3.2 years [IQR 3.0-4.3] for the sodium thiosulfate group, and 4.1 years [3.1-4.5] for the control group), but overall survival was significantly lower in the sodium thiosulfate group compared with the control group (median follow-up 3.2 years [3.0-4.5] for the sodium thiosulfate group, and 3.8 years [3.1-4.5] for the control group; FIG. 3). 3-year event-free survival was 42% (95% CI 21-61) in the sodium thiosulfate group versus 61% (39-77) in the control group; 3-year overall survival was 45% (23-65) versus 84% (62-94). In participants with disseminated disease, 12 events and 11 deaths occurred in the sodium thiosulfate group and ten events and four deaths occurred in the control group. Study data showing patient demographics, hearing loss in both treatment arms, and Kaplan-Meier survival curves for the entire study in addition to results stratified by cancer subtype and patient age may be found in (FIGS. 2-35).

Example 2: Sodium Thiosulfate (STS) as an Otoprotectant to Reduce the Incidence of Cisplatin-induced Hearing Loss for Standard Risk Hepatoblastoma The study was designed as a multi-centre open label randomised phase III trial to test the efficacy of Sodium Thiosulphate (STS) in reducing ototoxicity in patients receiving Cisplatin chemotherapy for standard risk hepatoblastoma. A total of 52 centers participated in 11 countries worldwide including United Kingdom, France, Belgium, Japan, Italy, Spain, Australia, New Zealand, Ireland, Switzerland, and the United States. The control arm included cisplatin only treated patients and the test arm including cisplatin treated patients followed by administration of STS.

End-points

The primary end point of the study was the rate of Brock grade ≥1 hearing loss determined after end of trial treatment or at an age of at least 3.5 years, whichever was later. Secondary end-points included: response to preoperative chemotherapy, complete resection, complete remission, event free survival (EFS), overall survival (OS), toxicity as graded by CTCAE v 3.0, long-term renal clearance, and feasibility of central audiology review Patient Inclusion Criteria Patients were included in the study if they had a histologically confirmed newly diagnosed hepatoblastoma according to the following criteria:

Standard risk hepatoblastoma:
    Pre-treatment Tumour Extension (PRETEXT) I, II or III (see Pretext table below) Serum alpha-fetoprotein (AFP) >100 µg/L No additional PRETEXT criteria

|  | No. of patients | No of positive responses (%) | No of patients with a complete tumour resection incl OLT (%) | No. patients who died of surgical complications | No. of patients who died of disease | OS at 3 years |
| --- | --- | --- | --- | --- | --- | --- |
| Standard risk PRETEXT | 77 | 69 (90%) | 75 (97%) | 2 (3%) | 5 (6%) | 91% |
| I | 6 | 6 (100%) | 6 (100%) | — | — | 100% |
| II | 39 | 37 (95%) | 39 (100%) | 1 (3%) | 1 (3%) | 95% |
| III | 32 | 26 (81%) | 30 (94%) | 1 (3%) | 4 (13%) | 84% |

Age ≤18 years and >1 month

Written informed consent and national/local ethics committee and regulatory approval Centre/country willing and able to organize audiometry at minimum required quality standard Ability to comply with requirements for submission of material for central review (radiology, pathology and audiology)

For females of child-bearing potential, a negative pregnancy test prior to study treatment was required Any patient who was of reproductive age had to agree to use adequate contraception for the duration of the trial (males had to always use a condom and females had to ensure their partner used a condom, and used one additional method of contraception for the duration of the period of chemotherapy)

Patient Exclusion Criteria

Patients were excluded from the study if they met any of the following exclusion criteria:

High risk hepatoblastoma:
Serum—Alpha-fetoprotein (AFP)≤100 µg/L
Tumour involving all 4 hepatic sections—PRETEXT IV
Additional PRETEXT criteria
Extrahepatic abdominal disease (E1, E1a, E2, E2a)
Intraperitoneal haemorrhage or tumour rupture (H1)
Distant metastases, any site (M1)
Lymph node metastases (N1, N2)
Involvement of the main portal vein (P2, P2a)
Involvement of all three hepatic veins and/or the IVC (V3, V3a)
Hepatocellular carcinoma Treatment starting more than 15 days from written biopsy report Abnormal renal function defined as calculated GFR <75% of the lower limit of normal for age at diagnosis, which over 2 years of age is <60 ml/min/1.73 m²

Any previous chemotherapy

Recurrent disease

Previous hypersensitivity to STS

Patient unable to follow the protocol for any reason

Randomization

Figure 36:
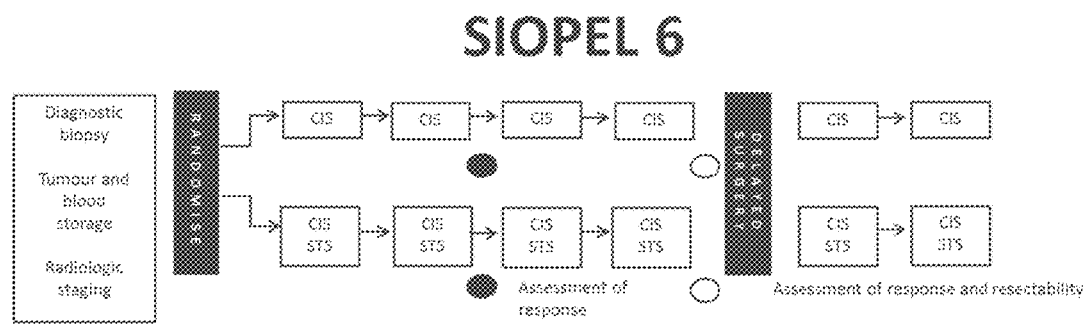
FIG. 36 is a schematic showing the study design for the study of Example 2.
Figure 37:
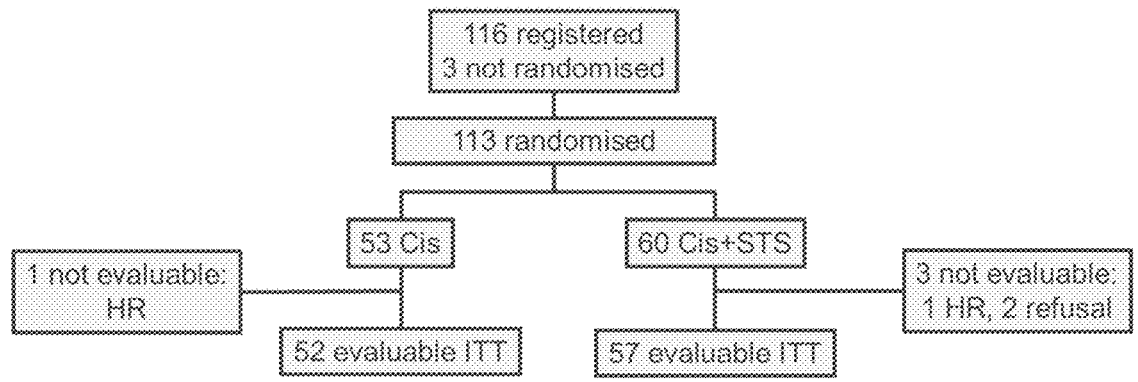
FIG. 37 is a flow diagram of patient eligibility and testing arms, either control or STS treated and the number of patients included at primary endpoint analysis for the study of Example 2.

Patients that met the above eligibility criteria were enrolled and randomly assigned to either the Sodium Thiosulfate or observation (control group) prior to receiving Cisplatin. The randomization and patient enrollment diagrams are provided in FIGS. 36 and 37. The enrolled patient characteristics were provided in FIG. 38.

Trial treatment

The Investigational Medicinal Products (IMPs) studied in this trial were Sodium Thiosulphate (STS) and Cisplatin. STS was provided by Adherex Technologies. Trial treatment consisted of the following phases:

Pre-operative randomised 1:1 chemotherapy (4 courses of Cisplatin, with or without STS, every second week)

Surgical removal of all remaining tumour lesions. If surgery has to be delayed, 1 or 2 cycles of the post-operative chemotherapy may be given pre-operatively.

Post-operative chemotherapy (2 courses of Cisplatin, with or without STS, every second week)

Patients with progressive disease after 2 or more courses of Cisplatin, with or without STS, discontinued trial treatment Treatment and Follow-up Plan Pre-operative chemotherapy, 4 courses Cisplatin +/− STS Definitive surgery after pre-operative chemotherapy (as in all previous SIOPEL trials)

Post-operative chemotherapy, 2 courses Cisplatin +/− (this can be given pre-operatively if surgery has to be delayed for valid practical reasons)

Long-term follow-up

Treatment Failure

Treatment was stopped in patients with progressive disease after 2 or more courses of Cisplatin with or without STS No further STS 2-4 courses Cisplatin-Doxorubicin (PLADO) were recommended, followed by definitive surgery when the response was sufficient Ideally 2 courses Chemotherapy Guidelines and Administered Treatments Cisplatin Cisplatin was supplied in 10 ml, 50 ml and 100 ml vials containing a 1 mg/ml solution formulations and optionally as a powder for reconstitution in 50 mg vials. Stability of the Cisplatin formulation followed the following:

Pre dilution: as per manufacturer's Summary of Product Characteristics

Post dilution: Cisplatin could be stable for up to a maximum of 7 days in a solution of sodium chloride. The manufacturer's Summary of Product Characteristics was followed.

Sodium Thiosulphate (STS) Source and Pharmacology

STS is a water-soluble thiol compound with reducing agent properties. Following IV injection, sodium thiosulphate was distributed throughout the extracellular fluid. Some Sodium Thiosulphate was converted to sulphate in the liver. Up to 95% was excreted unchanged in the urine. The biological half-life was 0.65 hours (range: dependent on dose 16.5-182 minutes).

Packaging and Labelling

Each vial was placed into a six vial kit box. Each box was labelled with a multi-language kit label. STS drug product was manufactured, labelled, and packaged under GMP conditions and supplied as a 25% (250 mg/mL), preservative free, sterile solution. The drug product formulation contained sodium thiosulfate pentahydrate and sodium borate. The vial label indicated the drug product batch number and the initial release until date.

Preparation

STS was supplied in 50 ml vials containing a 25% (250 mg/ml or 12.5 g/vial) solution. Each ml of the 25% STS was diluted with one ml of sterile water for injection (1:1 dilution) to a concentration of 125 mg/ml for direct administration. (This is approximately equivalent isotonicity to a 2.3% sodium chloride solution). The volume from the appropriate number of vials for the dose was combined in a PVC IV infusion bag.

Reconstituted STS for administration consisted of a clear solution. There were no preservatives in the formulation. After dilution the PVC infusion bag containing the dosing solution was placed upside down (inverted with injection and filling ports at the top) at room temperature and used within eight hours. Any solution remaining in the vial was destroyed according to institutional procedures.

Treatment Schedule

For all patients, the pre-surgery courses were given on day 1, 15, 29 and 43 (exceptionally, if surgery was delayed, courses could also be given on day 57 and 71). Post-surgery courses were started as soon as possible, but within 21 days with two courses given on day 1 and 15. Prior to starting each cycle of chemotherapy, the following measurements were established: whether the child had a good urine output, serum electrolytes and creatinine within the normal range for age and stable blood pressure <$97^{th}$ percentile for age, normal neurology and whether the child was febrile. The following treatment schedules were followed:

Cisplatin

| | |
|---|---|
| For children > 10 kg: | 80 mg/m² IV infusion over 6 hours |
| For infants and children 5-10 kg: | 2.7 mg/kg IV infusion over 6 hours |
| For infants < 5 kg: | 1.8 mg/kg IV infusion over 6 hours |

Sodium Thiosulphate

For children randomised to receive STS:

| | |
|---|---|
| For children > 10 kg: | 20 g/m² IV infusion over 15 minutes |
| For infants and children 5-10 kg: | 15 g/m² IV infusion over 15 minutes |
| For infants < 5 kg: | 10 g/m² IV infusion over 15 minutes |

Administration

Pre-hydration
- At least 3 hours pre-hydration with 2.5% dextrose/0.45% saline
- Run at 200 ml/m2/hr (total volume 600 ml/m²)

Cisplatin infusion over 6 hours
- Cisplatin in 0.9% sodium chloride. Suggested volume for infusion over 6 hours:
  - <60 mg in 60 ml, 60 mg-120 mg in 120 ml and >120 mg in 240 ml
- No fluids other than sodium chloride were used as a vehicle for Cisplatin in order to prevent chloride depletion, which would lead to increased risk for nephrotoxicity.

Hydration During and until 6 Hours Post Cisplatin (i.e. 12 Hours in Total)
- 2.5% Dextrose/0.45% sodium chloride
- Plus 6 g mannitol per 500 ml
- Plus 10 mmol potassium chloride per 500 ml
- Run at 125 ml/m2/hr Sodium Thiosulphate 6 Hours Post Cisplatin
- Diluted each ml of the 25% STS with 1 ml of sterile water for injection (1:1 dilution) to a concentration of 125 mg/ml for direct administration. (This has an approximately equivalent iotonicity to a 2.3% sodium chloride solution)
- Infused over 15 minutes
- Stopped the Cisplatin hydration fluid for 15 minutes during the STS infusion. Restarted the Cisplatin hydration immediately afterwards Hydration for Subsequent 18 Hours (i.e. Until 24 Hours after the End of Cisplatin Infusion)
- 2.5% Dextrose/0.45% sodium chloride
- Plus 10 mmol potassium chloride per 500 ml
- Plus 5 mmol magnesium sulphate per 500 ml
- Plus 0.3 mmol calcium gluconate per 500 ml
- Run at 125 ml/m2/hr Summary
- −3 hr start pre-hydration
- 0 hr finish pre-hydration, start Cisplatin infusion+hydration over 6 hours
- 6 hr finish Cisplatin infusion, continue with hydration for a further 6 hours
- 12 hr finish hydration, start STS infusion
- 12 hr 15min finish STS infusion, start post hydration
- 30 hr 15min finish post hydration A Bedside Nursing Work Sheet was provided to assist with the timings of Cisplatin, Sodium Thiosulphate (STS), hydration and anti-emetic administration. The worksheet was adapted to suit local practice. Paper copies of the worksheet were kept in the child's notes ready to be filled in when chemotherapy was given. The worksheet also included a table to record blood pressure and electrolyte monitoring for patients receiving STS.

Toxicity Monitoring

The trial treatment was recognized to be potentially toxic and children were at risk of developing myelo-, mucosal- or other reversible toxicity as well as irreversible oto- and renal toxicity. Therefore, toxicity monitoring was required for each child throughout trial treatment and at regular follow-up intervals. The reporting of specific renal and oto-toxicity was required as an adverse event. Serious Adverse Events was reported immediately on knowledge of the event. The trial committee evaluated toxicity reports on a regular basis and was authorized to stop the trial if an unacceptable rate of severe toxicity was recognized. The dose and treatment modifications due to toxicity were specified in the protocol. In addition, long-term follow up of patients in this trial were to include any late toxicity. The occurrence of adverse events is shown in FIG. 39.

Adverse drug reactions were monitored and defined as adverse events, which are possibly, probably or definitely related to the trial treatment and were assessed according to NCI CTCAE v 3.0. A Serious Adverse Event was defined—in accordance with the ICH Harmonised Tripartite Guideline for Good Clinical Practice definitions and additionally—as any untoward medical occurrence that: results in death (NB: death by tumour progression is not considered an SAE for these patients). A serious adverse event is one that is life-threatening, requires inpatient hospitalization or prolongation of existing hospitalization, leads to progression of disease, is an overdosage, is a second primary malignancy, results in persistent or significant disability/incapacity, is a congenital anomaly, any unexpected grade 3 and 4 toxicity Definition of Study Completion The primary endpoint was reached when the last patient completed his/her audiological testing or reached 3.5 years of age, whichever was later. Patients were then followed up for the secondary endpoints according to national guidelines Audiometry This trial was aimed at reducing ototoxicity in very young patients with hepatoblastoma. In order not to have to refuse patients entry into the trial, the end point only required pure tone audiometry to be carried out at the age of 3.5 years when the child is off treatment. In some cases this meant that the child moved to another centre to be tested.

In order to make central review meaningful all audiologic evaluations were completed using standard clinical audiometers, middle ear analyzers, and evoked Otoacoustic Emission (OAE) systems. All equipment was calibrated in accordance with international guidelines. Baseline hearing evaluations were completed before the first dose of Cisplatin whenever possible. Definitive audiologic evaluation was completed for all children at the age of 3.5 years (or as soon as a reliable hearing test could be obtained). The minimum criteria for entry into this trial was that Pure Tone Audiometry could be completed, together with otoscopy and tympanometry, at the end of treatment directly or when the child reached the age of 3.5 years, if younger at the end of treatment. The audiological testing was required to take place in a competent department familiar with testing young children. The parents agreed in writing, on the trial consent form, to travel to a centre, in another town in their country, if necessary, in order to get this done. The end of treatment audiological review was then provided for central review. All participating centres were asked to give contact details of the Consultant Audiologist or Ear Nose and Throat Surgeon who was responsible for coordinating and overseeing the quality of the centre considered competent to carry out this end of treatment audiological assessment in their country.

Audiologic evaluations included: Measurement of bilateral pure tone air conduction thresholds at 8, 6, 4, 2, 1 and 0.5 kHz starting with the high frequencies, otoscopy, Immittance evaluation or tympanometry, measurement of TEOAEs and DPOAEs at facilities where this equipment was available. If a child was uncooperative or too unwell to give reliable responses on behavioural assessment and had middle ear effusion and hence TEOAE and DPOAE could not be done then thresholds were obtained using bone conduction auditory brainstem response (ABR). Ideally using tone burst, but click evoked ABR would also be helpful Procedures for obtaining pure tone thresholds included standard behavioural measurement techniques appropriate for the age and development of the child, including conditioned play audiometry and visual reinforcement audiometry. During the study, a descending testing procedure, starting at 8000 Hz, was recommended for all children and was especially important for children with limited cooperation, as any decrease in auditory sensitivity will most likely occur at the higher frequencies. Obtaining 0.5 kHz was recommended as tester could reassess reliability of responses. Inserted earphones or headphones were used to obtain ear-specific thresholds whenever possible. Bone conduction thresholds were measured if baseline testing indicated pre-existing hearing loss, if a child had a significant decrease in hearing at the definitive evaluation, and/or if immittance results indicated conductive middle ear pathology. When behavioural test results could not be reliably obtained, auditory thresholds were estimated using an electrophysiologic test procedure, specifically click or tone burst evoked ABR.

Immittance evaluation included the measurement of middle ear pressure and compliance and acoustic reflex thresholds. Probe tones were equal to or greater than 660 Hz instead of 226 Hz in babies. Tympanograms were classified as normal if the static admittance is 0.2 mmho or greater, the peak pressure between −150 to +200 daPa, and the tympanometric width less than 160 daPa. Acoustic reflex thresholds were measured at 500, 1000, 2000 and 4000 Hz ipsilaterally in both ears.

Transient Evoked Otoacoustic Emissions (TEOAEs) and Distortion Product Otoacoustic Emissions (DPOAE)s were collected at facilities when the equipment was available. If a child exhibited evidence of active middle ear disease, as evidenced by abnormal tympanometry and/or conductive hearing loss, Otoacoustic Emission (OAE) measurement was deferred until the middle ear pathology resolved. For TEOAEs click stimuli was presented at 80 dB peak equivalent SPL. The two TEOAE parameters that were used to compare results was total emissions level (mean response) and the reproducibility of the waveforms in the frequency region 1000-4000 Hz. For DPOAEs one level of L1 and L2 65/55 dB SPL was done at least at four frequencies. TEOAE is regarded as a better predictor of low frequency and DPOAE of high frequency sensitivity.

The following test protocols were used based upon the age of the pediatric patient: Evaluation for children younger than 12 months of age included: Measurement of minimal thresholds by visual reinforcement audiometry (VRA) preferably with insert ear phone, if the child did not accept that, then on sound field setting with dBA weighting was converted to equivalent of hearing level (HL) by the central audiology committee through the to equate to pure tones. In addition, tympanometry, and the measurement of TEOAEs and DPOAEs was carried out. Click or tone burst evoked ABRs were used to estimate auditory thresholds if possible. If ABR was not available, acoustic reflex thresholds was measured.

Evaluation for children younger than 12-42 months of age included: Evaluation by VRA or conditioned play audiometry, if thresholds were estimated on sound field setting in dBA weighting was converted to HL. In addition, tympanometry, and the measurement of TEOAEs and DPOAEs was carried out. Click or tone burst evoked ABRs were used to estimate auditory thresholds if possible. If ABR was not available, acoustic reflex thresholds was measured. If reliable results could not be obtained by behavioural testing, then ABR or acoustic reflex threshold measurement was recommended.

Evaluation for children 3.5 years and older included: Evaluation using play audiometry as described above or standard pure tone threshold. addition, tympanometry, and the measurement of TEOAEs and DPOAEs was carried out.

Guidelines for visual reinforcement audiometry (VRA) included visual reinforcement audiometry is the standard accepted method for obtaining frequency and ear specific hearing thresholds in children between the ages of 6 months through 30 months. Animated and/or lighted toys are used to condition and reinforce a head-turning response to sound. Insert earphones should be used whenever possible. If a child will not tolerate wearing earphones, testing may be completed using warbled pure tone presented through calibrated sound field speakers. These thresholds measured as dBA should be converted to dB HL for purpose of this study.

Guidelines for auditory brainstem response (ABR) included testing for air conduction (AC) threshold estimation is difficult in very young children who will not cooperate for behavioural assessment or for OAEs. Measurement of auditory evoked brainstem potentials is an electrophysiologic procedure, which allows for evaluation of peripheral auditory function and threshold determination in subjects who are not able to participate in behavioural testing due to cooperation or state of health. Although ABR does not measure hearing sensitivity, ABR thresholds are strongly correlated with thresholds of hearing sensitivity and allow for an estimation of auditory thresholds.

Frequency specific tone burst stimuli were used to measure ABR thresholds whenever possible for 500, 1000, 2000, and 4000 Hz stimuli. Thresholds for click stimuli were obtained if evaluation with frequency specific stimuli is not available. ABR thresholds will be determined as the lowest level at which detectable, repeatable wave V responses are obtained. Responses were labelled only when replicable and compared with normative paediatric data. Frequency specific stimulus, i.e. tone burst low, mid and high frequency or click evoked ABR, is delivered via earphones. If the AC thresholds were raised, i.e. greater than 20 dB nHL or where due to time constraints it is not possible to do full audiological evaluation, then bone conduction (BC) testing was carried out to determine the thresholds of the better hearing ear. Thresholds should be determined using 10 dB steps down to 20 dB nHL. All thresholds obtained in dB nHL were converted to HL using the conversion table.

Guidelines for OAE

Otoacoustic emissions are sounds that are produced by healthy ears in response to acoustic stimulation. They are byproducts of the activity of the outer hair cells in the cochlea. OAEs are measured by presenting a series of very brief acoustic stimuli, clicks, to the ear through a probe that is inserted in the outer third of the ear canal. The probe contains a loudspeaker that generates clicks and a microphone that measures the resulting OAEs that are produced in the cochlea and are then reflected back through the middle ear into the outer ear canal. The resulting sound that is picked up by the microphone is digitized and processed by specially designed hardware and software. The very low-level OAEs are separated by the software from both the background noise and from the contamination of the evoking clicks.

Monitoring During Treatment

After the initial baseline audiologic evaluation as recommended before start of treatment, interim audiometry was recommended after every second cycle of Cisplatin. In children younger than 3.5 years of age interim audiometry was strongly recommended.

All children had a definitive evaluation when they completed treatment and were aged 3.5 years or older. If the child was old enough the evaluation was done within 6-12 weeks after the last Cisplatin dose. Ototoxicity was assessed using Brock grading as defined herein, as well as ASHA guidelines wherever pre-chemotherapy hearing thresholds were available. If the children had hearing loss equal to or greater than Brock's grade 1 on the definitive audiologic evaluation, that was considered as positive for ototoxicity.

Wherever ASHA criteria could be applied, ototoxicity was defined as positive when there is a hearing loss of: 20 db decrease at any one test frequency or 10 db decrease at any two adjacent frequencies or loss of response at three consecutive test frequencies where responses were previously obtained (this refers to high frequencies) as described by ASHA criteria. In cases of asymmetric hearing loss, results will be reported for both ears.

All audiologic data was centrally reviewed. The data was collected on each child and was submitted in HL weighting. Data was submitted for central review as soon as possible after the tests have been performed. ASHA criteria and OAE guidelines and Brock grading guidelines followed in this study are described below.

Brock Grading and ASHA Criteria

Brock grading

The Brock grading system was used to monitor Cisplatin-induced bilateral high-frequency hearing loss (grades 1-4)

| BILATERAL REARING LOSS | GRADE | Designation |
| --- | --- | --- |
| <40 dB at all frequencies | 0 | Minimal |
| ≥40 dB at 8,000 Hz only | 1 | Mild |
| ≥40 dB at 4,000 Hz and above | 2 | Moderate |
| ≥40 dB at 2,000 Hz and above | 3 | Marked |
| ≥40 dB at 1,000 Hz and above | 4 | Severe |

ASHA Criteria and Guidelines:

From the American Speech-Language-Hearing Association Guidelines for the audiologic management of individuals receiving cochleotoxic drug therapy and Guidelines for the audiologic assessment of children from birth to 5 years of age.

Elements of Monitoring:

The cochleotoxicity monitoring programme at study locations required (a) specific criteria for identification of toxicity, (b) timely identification of at-risk patients, (c) pre-treatment counselling regarding potential cochleotoxic effects, (d) valid baseline measures (pre-treatment or early in treatment), (e) monitoring evaluations at sufficient intervals to document progression of hearing loss or fluctuation in sensitivity, and (f) follow-up evaluations to determine post-treatment effects.

Audiometric Criteria for Cochleotoxicity:

In this study, criteria were constructed to identify and detect the most cases of true ototoxicity. The criteria were set to be conservative, because an occasional false-positive identification was preferable to other methods, which could delay detection of the ototoxic process.

In a study of normal test-retest variability of audiometric thresholds normal variability was reflected by independent shifts at random frequencies. Thus, shifts at adjacent test frequencies are known to indicate more systematic change and increase the likelihood of a true decrease in sensitivity. Frequency averaging (i.e. calculating the average of thresholds across some frequency range) has been advocated for detecting decreased sensitivity, and the use of adjacent frequencies is equivalent to averaging over those frequencies. Another fundamental concept is that a decrease, observed on repeated tests, is a valid change. Thus, a shift relative to baseline that was observed at least twice is likely to represent a true shift and not normal variation.

Change in hearing sensitivity was computed relative to baseline measures. Criteria to indicate hearing decrease during ototoxicity monitoring were defined as (a) 20 dB decrease at any one test frequency, (b) 10 dB decrease at any two adjacent frequencies, or (c) loss of response at three consecutive test frequencies where responses were previously obtained (the third criterion refers specifically to the highest frequencies tested, where earlier responses are obtained close to the limits of audiometric output and later responses cannot be obtained at the limits of the audiometer). Finally, any change was confirmed by repeat testing.

Baseline Testing

Patient hearing was tested at baseline. The purpose of the baseline testing was to document the status of hearing prior to treatment. At-risk individuals received baseline evaluations, which were as complete as possible. Word discrimination was recommended to be included in the ideal scope of audiologic practice. The reliability of behaviour responses was recommended to be assessed during baseline by repeating selected portions of the evaluation. In addition, results of the first test following baseline should be evaluated for inter- test reliability.

The optimal timing of baseline testing depends largely on the drug(s) the patient is receiving. For example, it is known that animals receiving large bolus doses of kanamycin do not show histologic evidence of cochleotoxicity until after 72 hours. Thus, in the absence of more precise data, baseline audiometric evaluation of patients receiving aminoglycosides should be done prior to or within 72 hours of first treatment dose. Cisplatin can cause observable cochleotoxicity following a single course of treatment. Thus, baseline measures were obtained prior to the first dose of Cisplatin.

Monitoring Schedule and Follow-Up Tests

Monitoring tests were scheduled at intervals that enabled the earliest possible detection (within reason) of cochleotoxic effects. Immediate post-treatment testing was suggested to document auditory status at the end of drug treatment. Follow-up testing was recommended to be completed at intervals appropriate to detect post-treatment cochleotoxicity or to document recovery.

ABR Testing for Threshold Estimation

Stimuli: Frequency-specific stimuli (tone bursts of low, mid and high frequency).

Transducer: Insert earphones were recommended, unless contraindicated, for air-conduction testing. A bone-conduction transducer was needed if air conduction is elevated (i.e. if air-conduction thresholds are greater than 20 dB nHL, bone-conduction testing was recommended to be completed to assess the type of hearing loss).

Protocol: Responses were attempted down to 20 dB nHL. Definition of threshold was attempted in at least 10 dB steps. Recording epochs of 20-25 ms were necessary for adequate ABR threshold detection measures in infants, especially when tonal stimuli were used. Many children in the age group birth to 4 months of age were tested during natural sleep, without sedation, using sleep deprivation with nap and feeding times coordinated around the test session. However, active or older infants in some cases required sedation to allow adequate time for acquisition of high-quality recordings and sufficient frequency-specific information.

Otoacoustic Emissions (OAEs)

Limited

Transient Evoked Otoacoustic Emission (TEOAE): One level (e.g. 80 dB pSPL) click stimulus was completed. Normal distributions for this condition for normal hearing are known (see Hussain DM, Gorga MP, Neely S T, Keefe D H, Peters J. Transient evoked otoacoustic emissions in patients with normal hearing and in patients with hearing loss. *Ear Hear* 1998; 19(6):434-49).

Distortion Product Otoacoustic Emission (DPOAE): One level of $L_2$ and $L_2$ 265/55 dB SPL at least at four frequencies. Normal distributions for this condition are known (see Gorga MP, Neely S T, Ohlrich B, Hoover B, Redner J, Peters J. From laboratory to clinic: a large scale study of distortion product otoacoustic emissions in ears with normal hearing and ears with hearing loss. *Ear Hear* 1997;18(6):440-55).

Comprehensive

TEOAE: Two levels (e.g. 80 dB pSPL and a lower level) were completed and/or one level using click and multiple frequencies for stimuli, or DPOAE: Use of three levels (e.g., 65/55 and lower levels, as shown by Kummer et al (18-19) were completed to obtain DPOAE input-output functions, or at one level for multiple (more than four) frequencies, or Comparison of TEOAE (e.g., single level, single stimulus) and DPOAE (e.g., single level): The TEOAE is a better predictor of low-frequency hearing sensitivity and the DPOAE is a better predictor of high-frequency sensitivity.

Acoustic Immittance Assessment

Probe tones equal to or greater than 660 Hz were used because of the poor validity of tympanometry when using a low-frequency probe tone with this age group and the demonstrated diagnostic value of tympanometry with a high-frequency probe tone.

Unresponsive Patients

In non-responsive patients, objective hearing measures (e.g. auditory evoked potentials and evoked otoacoustic emissions) was the only means to obtain auditory information. Although objective procedures provide only gross information on hearing sensitivity, they are nonetheless, capable of detecting ototoxic hearing loss.

Criteria of Tumor Evaluation

For all endpoints, all treated patients (i.e. who received at least one dose of trial medication) were analyzed for evaluation of response to pre-operative chemotherapy and tumour status at the end of trial treatment. Responses to treatment were defined as follows: Complete response (CR): no evidence of disease and normal serum AFP value (for age). Partial response (PR): any tumour volume shrinkage associated with a decreasing serum AFP value, >1 log below the original measurement. Stable disease (SD): no tumour volume change and no change, or <1 log fall of the serum AFP concentration. Progressive disease (PD): unequivocal increase in 1 or more dimensions and/or any unequivocal increase of the serum AFP concentration (three successive 1-2 weekly determinations) even without clinical (physical and/or radiological) evidence of tumour re-growth.

Tumor relapse was defined as follows: Recurrent tumour lesion(s) (local or metastatic) detected by imaging techniques and serial elevation of serum AFP (at least 3 consecutive rising values, taken at weekly intervals). In these patients biopsy of the tumour was recommended but not compulsory. Recurrent tumour lesion(s) (local or metastatic) with normal AFP, histologically confirmed by biopsy.

Overall survival was calculated from the time of randomization to death. Event free survival will be calculated from the time of randomization to the first of the following events: progression, relapse, secondary primary malignancy or death.

Statistical Considerations

The trial was designed to detect a 25% reduction in the rate of Brock grade ≥1 hearing loss with a chi-square test, from a 60% hearing loss in the Cisplatin alone arm to a 35% hearing loss in the Cisplatin +STS arm. The study was statistically powered to answer the main objective of the trial, which was to investigate if the administration of STS simultaneously with the administration of Cisplatin significantly reduces the hearing impairment at the age of The results of the primary endpoint analysis was presented as rates with 95% confidence interval (CI), and as a relative risk with 95% CI. In addition, audiograms were evaluated in detail. Time to event endpoints were presented as Kaplan-Meier estimators and corresponding graphs. Overall survival (OS) and event free survival (EFS) were analyzed in an exploratory fashion by multivariate Cox regression taking into account potential prognostic factors. Rates were compared by chi-square test or Fisher's exact test as appropriate.

The final analysis was completed once a definitive assessment of hearing impairment was available for 102 patients, or 3 years after the last patient was enrolled. OS and EFS endpoints were evaluated at the study end point and will be continued to be evaluated up to a follow-up of at least 5 years from the enrolment of the last patient.

Results

Figure 40:
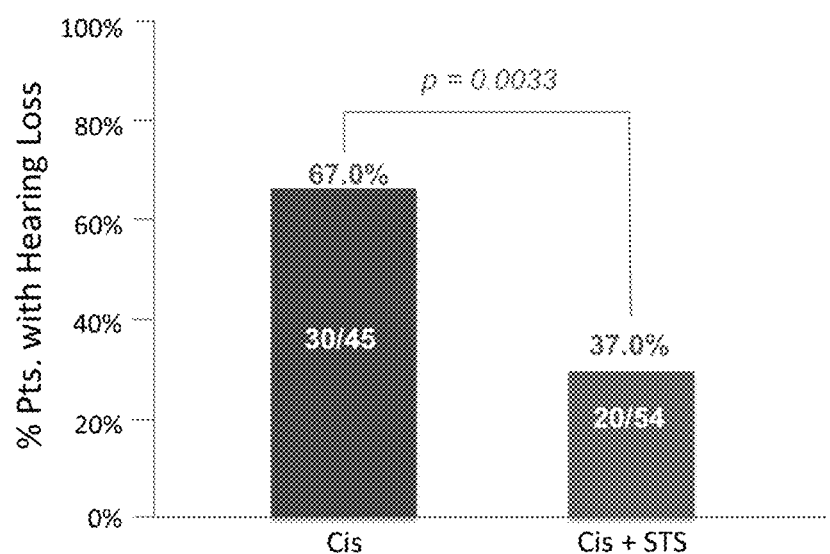
FIG. 40 is a bar graph showing the hearing results according to Brock grade ≥1 by treatment arm, either cisplatin or cisplatin +STS for the study of Example 2.
Figure 41:
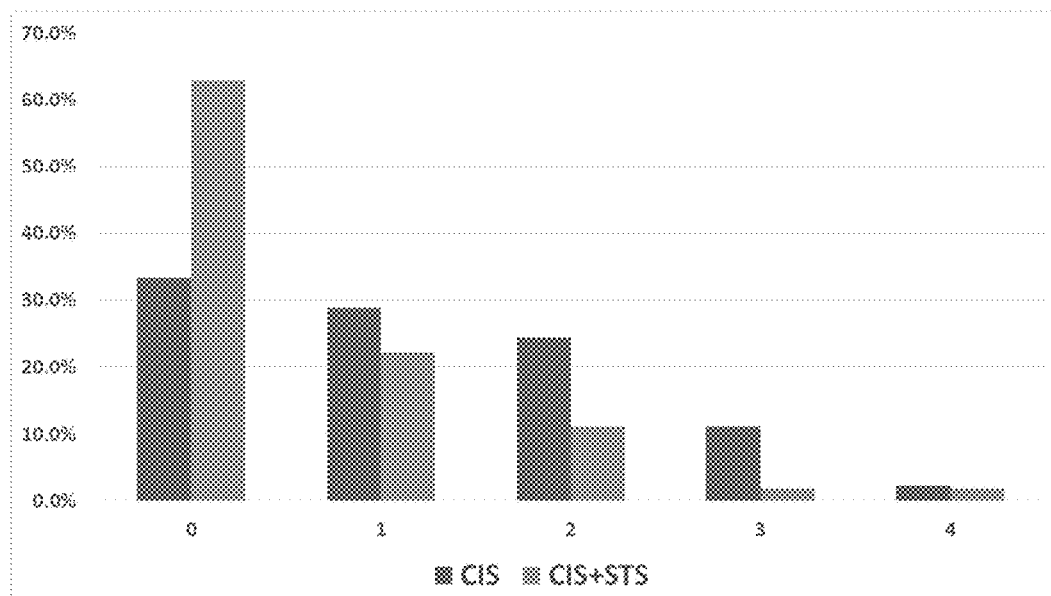
FIG. 41 is a bar graph showing the hearing results according to Brock grades 0-4 by treatment arm, either cisplatin or cisplatin +STS for the study of Example 2.
Figure 42A:
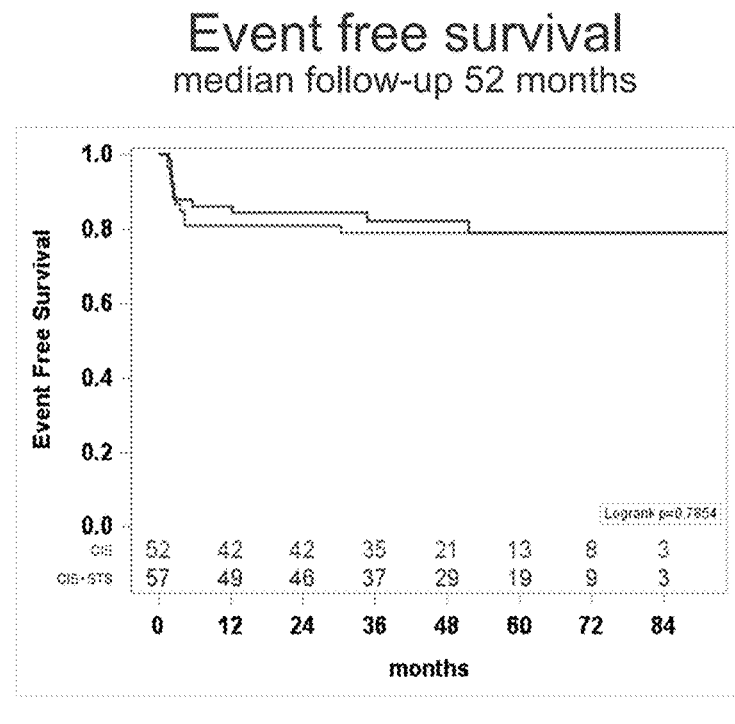
FIG. 42A is a Kaplan-Meier curve showing analysis of event free survival of patients separated by treatment arm for enrolled in the study of Example 2; the median follow-up time was 52 months.
Figure 42B:
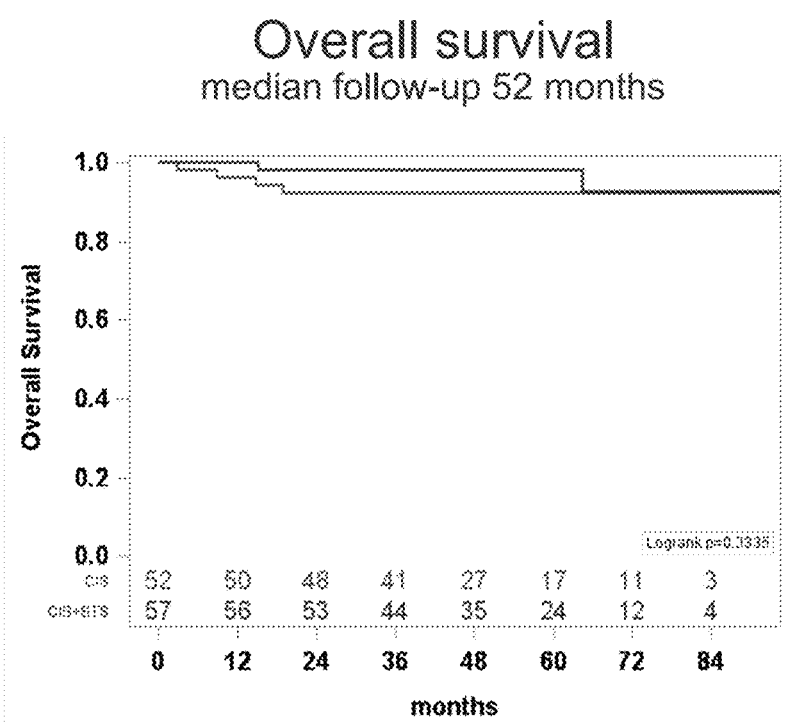
FIG. 42B is a Kaplan-Meier curve showing analysis of overall survival of patients separated by treatment arm for enrolled in the study of Example 2; the median follow-up time was 52 months.

Upon completion of the study, it was determined that patients having hepatoblastoma that were treated with cisplatin but not STS had an incidence rate of Brock ≥1 hearing loss of 67%. Treatment with STS greatly reduced this number by about half to 37% (p value=0.0033; 95% CI; see FIG. 40). Conversely, patients having Brock grade 0 or little to no hearing loss was above 60% for the STS arm and below 40% for the cisplatin treatment only arm of the study. The reduction hearing loss was most dramatic for Brock grade 2 and grade 3 hearing loss, which represents a significant decline in hearing function, that treatment with STS was able to prevent (see FIG. 41). After a median 52 month follow-up, no differences in either of event free survival or relapse free survival was observed for either treatment arm (see FIGS. 42A and 42B).

These results indicate that STS was able to significantly reduce hearing loss in pediatric patients having hepatoblastoma. The reduction in hearing loss was most pronounced for Brock grade 2 and 3 patients, indicating that STS is able to prevent significant declines in hearing in these pediatric patients.

What is claimed is:

1. A method of reducing ototoxicity in a pediatric patient of about 5 years of age and under, comprising: administering:
   (I) cisplatin to treat a localized and non-metastatic tumor at a dose of about 1 mg/kg to about 5 mg/kg or about 10 mg/m$^2$ to about 300 mg/m$^2$ per cycle, administered on between about 1 and 5 days per cycle; and
   (II) sodium thiosulfate, at a dose of about 5 g/m$^2$ to about 25 g/m$^2$ given after each dose of the cisplatin on between about 1 and 5 days per cycle, about six hours after the administration of the cisplatin,
wherein the reduction of ototoxicity is at least 50% better than a patient not receiving an administration of sodium thiosulfate;
wherein ototoxicity is determined by one or more criteria selected from:
a) a reduction in hearing measured by a 20 dB loss at a single frequency;
b) a reduction in hearing measured by a 10 dB loss at two consecutive frequencies;
c) loss of response at three consecutive test frequencies where responses were previously obtained;
d) a reduction in bilateral high-frequency hearing characterized by the criteria:
   i) a <40 dB hearing loss at all frequencies, which indicates a grade 0 or minimal hearing loss;
   ii) a ≥40 dB hearing loss at 8,000 Hz only, which indicates a grade 1 or mild hearing loss;
   iii) a ≥40 dB hearing loss at 4,000 Hz and above, which indicates a grade 2 or moderate hearing loss;
   iv) a ≥40 dB hearing loss at 2,000 Hz and above, which indicates a grade 3 or marked hearing loss;
   v) a ≥40 dB hearing loss at 1,000 Hz and above, which indicates a grade 4 or severe hearing loss; or
e) a reduction in hearing characterized by the criteria:
   i) a ≤20 dB hearing loss at all frequencies, which indicates a grade 0 hearing loss;
   ii) a >20 dB HL above 4,000 Hz, which indicates a grade 1 hearing loss;
   iii) a >20 dB HL at 4,000 Hz and above, which indicates a grade 2 hearing loss;
   iv) a >20 dB HL at 2,000 Hz or 3,000 Hz, which indicates a grade 3 hearing loss;
   v) a >40 dB HL at 2,000 Hz and above, which indicates a grade 1 hearing loss;
wherein a change in hearing is computed relative to baseline measures prior to the patient receiving a platinum based chemotherapeutic or sodium thiosulfate or both; and
wherein the administration of sodium thiosulfate does not substantively affect relapse free survival or overall survival compared to a pediatric patient not administered sodium thiosulfate.

* * * * *

(12) INTER PARTES REVIEW CERTIFICATE (3171st)
United States Patent
Neuwelt

(10) Number: US 10,596,190 K1
(45) Certificate Issued: Jul. 5, 2023

(54) METHOD FOR REDUCING OTOTOXICITY IN PEDIATRIC PATIENTS RECEIVING PLATINUM-BASED CHEMOTHERAPY

(71) Applicant: Edward A. Neuwelt

(72) Inventor: Edward A. Neuwelt

(73) Assignee: THE UNITED STATES GOVERNMENT DEPARTMENT OF VETERANS AFFAIRS

Trial Number:

IPR2022-00123 filed Oct. 29, 2021

Inter Partes Review Certificate for:

Patent No.: 10,596,190
Issued: Mar. 24, 2020
Appl. No.: 16/112,195
Filed: Aug. 24, 2018

The results of IPR2022-00123 are reflected in this inter partes review certificate under 35 U.S.C. 318(b).

INTER PARTES REVIEW CERTIFICATE
U.S. Patent 10,596,190 K1
Trial No. IPR2022-00123
Certificate Issued Jul. 5, 2023

AS A RESULT OF THE INTER PARTES REVIEW PROCEEDING, IT HAS BEEN DETERMINED THAT:

Claim 1 is cancelled.

\* \* \* \* \*